(12) United States Patent
Son et al.

(10) Patent No.: US 10,580,997 B2
(45) Date of Patent: Mar. 3, 2020

(54) CONDENSED CYCLIC COMPOUND AND ORGANIC LIGHT-EMITTING DEVICE INCLUDING THE SAME

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Jhunmo Son, Yongin-si (KR); Miyoung Chae, Suwon-si (KR); Dalho Huh, Suwon-si (KR); Eunsuk Kwon, Suwon-si (KR); Sangmo Kim, Hwaseong-si (KR); Hyunjung Kim, Suwon-si (KR); Youngmok Son, Hwaseong-si (KR); Namheon Lee, Suwon-si (KR); Saeyoun Lee, Suwon-si (KR); Soonok Jeon, Seoul (KR); Yeonsook Chung, Seoul (KR); Yongsik Jung, Yongin-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 181 days.

(21) Appl. No.: 15/585,829

(22) Filed: May 3, 2017

(65) Prior Publication Data

US 2017/0352819 A1 Dec. 7, 2017

(30) Foreign Application Priority Data

Jun. 2, 2016 (KR) .................. 10-2016-0068841

(51) Int. Cl.
*H01L 51/50* (2006.01)
*H01L 51/00* (2006.01)
(Continued)

(52) U.S. Cl.
CPC ...... *H01L 51/0072* (2013.01); *C07D 491/048* (2013.01); *C07D 495/04* (2013.01); *C09K 11/025* (2013.01); *C09K 11/06* (2013.01); *H01L 51/0071* (2013.01); *C09K 2211/1007* (2013.01); *C09K 2211/1044* (2013.01); *C09K 2211/185* (2013.01); *H01L 51/0085* (2013.01); *H01L 51/5016* (2013.01);
(Continued)

(58) Field of Classification Search
None
See application file for complete search history.

(56) References Cited

U.S. PATENT DOCUMENTS

2013/0234119 A1 9/2013 Mizuki et al.
2014/0158992 A1 6/2014 Xia et al.
(Continued)

FOREIGN PATENT DOCUMENTS

JP 2011-256143 A 12/2011
KR 10-2013-0084093 A 7/2013
(Continued)

*Primary Examiner* — Gregory D Clark
(74) *Attorney, Agent, or Firm* — Cantor Colburn LLP

(57) ABSTRACT

A condensed cyclic compound represented by Formula 1:

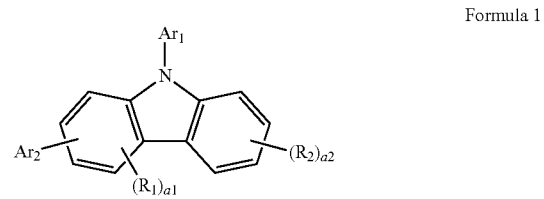

Formula 1 wherein in Formula 1, a1, a2, $Ar_1$, $Ar_2$, $R_1$, and $R_2$ are the same as described in the specification.

21 Claims, 1 Drawing Sheet

(51) Int. Cl.
*C07D 491/048* (2006.01)
*C07D 495/04* (2006.01)
*C09K 11/02* (2006.01)
*C09K 11/06* (2006.01)

(52) U.S. Cl.
CPC ...... *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(56) References Cited

U.S. PATENT DOCUMENTS

| | | | | |
|---|---|---|---|---|
| 2014/0225046 | A1* | 8/2014 | Jatsch | ............... C07D 405/14 252/519.3 |
| 2014/0364625 | A1* | 12/2014 | Ahn | ............... H01L 51/0072 548/418 |
| 2015/0105563 | A1 | 4/2015 | Ahn et al. | |
| 2015/0115205 | A1* | 4/2015 | Kang | ............... C07D 405/14 252/500 |

FOREIGN PATENT DOCUMENTS

| | | |
|---|---|---|
| KR | 10-2013-0112342 A | 10/2013 |
| KR | 10-2013-0127563 A | 11/2013 |
| KR | 10-2015-0047858 A | 5/2015 |
| WO | 2013-088973 A1 | 6/2013 |
| WO | 2013-127563 A1 | 9/2013 |
| WO | 2013-165189 A1 | 11/2013 |
| WO | 2014-204464 A1 | 12/2014 |

* cited by examiner

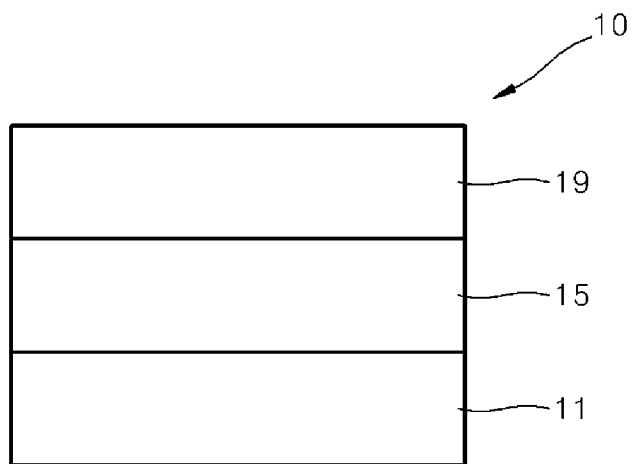

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0068841, filed on Jun. 2, 2016, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices have wide viewing angles, high contrast ratios, and short response times. In addition, organic light-emitting devices display excellent luminance, driving voltage, and response speed characteristics, and produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

According to an aspect of an embodiment, there is provided a condensed cyclic compound represented by Formula 1:

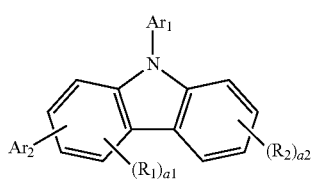

Formula 1

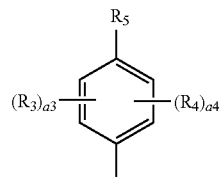

Formula 2A

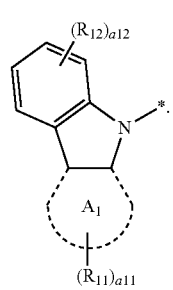

Formula 2B

In Formula 1, $Ar_1$ may be a group represented by Formula 2A, and $Ar_2$ may be a group represented by Formula 2B, ring $A_1$ in Formula 2B may be a dibenzofuran ring or a dibenzothiophene ring, $R_1$ to $R_3$, $R_{11}$, and $R_{12}$ in Formulae 1, 2A, and 2B may each independently be selected from:

hydrogen, deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one deuterium; and a phenyl group, a biphenyl group, a terphenyl group, a carbazolyl group, a pyridinyl group, a dibenzofuranyl group, a dibenzothiophenyl group, and a dibenzosilolyl group, each substituted with at least one selected from deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group, a1 and a3 in Formulae 1 and 2A may each independently be an integer selected from 0 to 3, wherein, when a1 is two or more, two or more groups $R_1$ may be identical to or different from each other, and when a3 is two or more, two or more groups $R_3$ may be identical to or different from each other, a2 and a12 in Formulae 1 and 2B may each independently be an integer selected from 0 to 4, wherein, when a2 is two or more, two or more groups $R_2$ may be identical to or different from each other, and when a12 is two or more, two or more groups $R_{12}$ may be identical to or different from each other, a11 in Formula 2B may be an integer selected from 0 to 6, wherein, when a11 is two or more, two or more groups $R_{11}$ may be identical to or different from each other, $R_4$ in Formula 2A may be selected from:

a phenyl group, a biphenyl group, and a terphenyl group;

a phenyl group, a biphenyl group, and a terphenyl group, each substituted with at least one selected from deuterium, a $C_1$-$C_{20}$ alkyl group, and a $C_1$-$C_{20}$ alkoxy group, a4 in Formula 2A may be an integer selected from 1 to 4, wherein a4 is two or more, two or more groups $R_4$ may be identical to or different from each other, $R_5$ in Formula 2A may be selected from:

hydrogen, deuterium, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one deuterium, and

* in Formulae 2A and 2B indicates a binding site to a neighboring atom.

According to another aspect of an embodiment, there is provided an organic light-emitting device including:

a first electrode;

a second electrode; and an organic layer disposed between the first electrode and the second electrode, wherein the organic layer includes an emission layer, and wherein the organic layer includes at least one condensed cyclic compound represented by Formula 1.

BRIEF DESCRIPTION OF THE DRAWING

These and/or other aspects will become apparent and more readily appreciated from the following description of the embodiments, taken in conjunction with FIG. 1, which is a schematic diagram of a structure of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to an aspect of the present inventive concept, a condensed cyclic compound is represented by Formula 1:

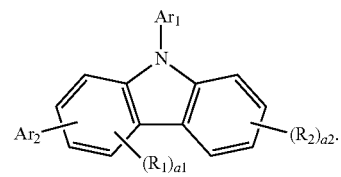

Formula 1

In Formula 1, $Ar_1$ may be a group represented by Formula 2A, $Ar_2$ may be a group represented by Formula 2B. Descriptions of Formulae 2A and 2B will be provided below:

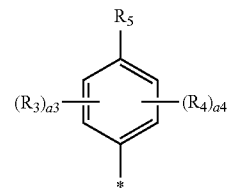

Formula 2A

-continued

Formula 2B

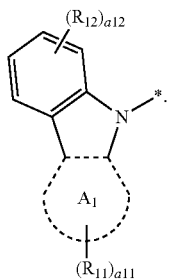

In an embodiment, Ar$_1$ in Formula 1 may be one selected from groups represented by Formulae 2A-1 to 2A-5, but embodiments are not limited thereto:

Formula 2A-1

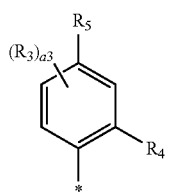

Formula 2A-2

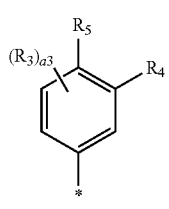

Formula 2A-3

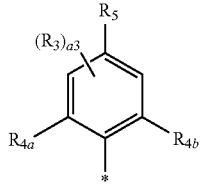

Formula 2A-4

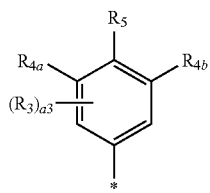

Formula 2A-5

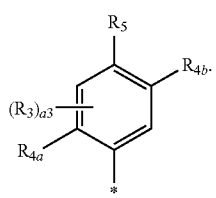

In Formulae 2A-1 to 2A-5,
R$_3$ to R$_5$ may each independently be the same as described elsewhere herein in connection with those provided in the present specification,
a3 may be an integer selected from 0 to 2,
R$_{4a}$ and R$_{4b}$ may each independently be the same as described herein in connection with R$_4$, and
* indicates a binding site to a neighboring atom.

In Formula 2B, ring A$_1$ may be a dibenzofuran ring or a dibenzothiophene ring.

In various embodiments, Ar$_2$ in Formula 1 may be one selected from groups represented by Formulae 2B-1 to 2B-6, but embodiments are not limited thereto:

Formula 2B-1

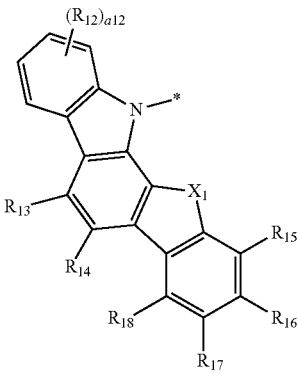

Formula 2B-2

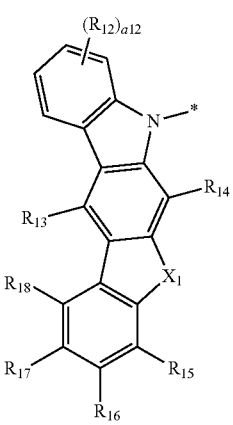

Formula 2B-3

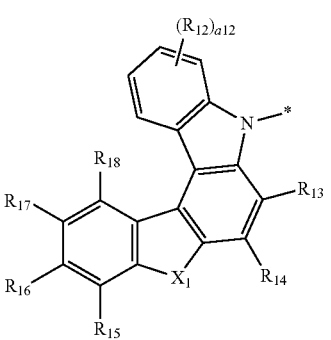

Formula 2B-4

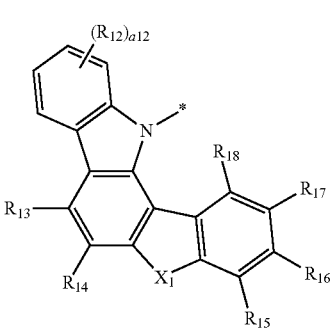

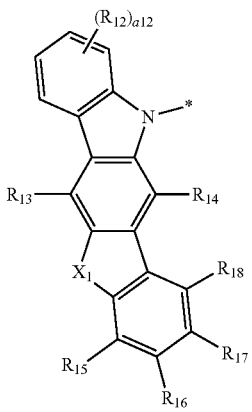

Formula 2B-5

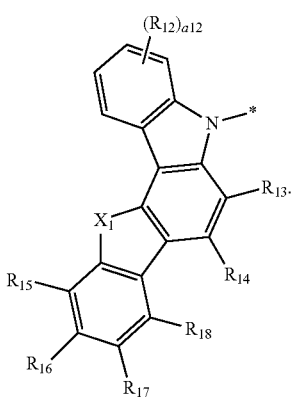

Formula 2B-6

In Formulae 2B-1 to 2B-6, $X_1$ may be O or S, $R_{12}$ and a12 may each independently be the same as described elsewhere herein in connection with those provided in the present specification, $R_{13}$ to $R_{18}$ may each independently be the same as described herein in connection with $R_{11}$, and

* indicates a binding site to a neighboring atom.

In Formulae 1, 2A, and 2B, $R_1$ to $R_3$, $R_{11}$, and $R_{12}$ may each independently be selected from:

hydrogen, deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one deuterium; and a phenyl group, a biphenyl group, a terphenyl group, a carbazolyl group, a pyridinyl group, a dibenzofuranyl group, a dibenzothiophenyl group, and a dibenzosilolyl group, each substituted with at least one selected from deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group.

In various embodiments, $R_1$ to $R_3$, $R_{11}$, and $R_{12}$ may each independently be selected from:

hydrogen, deuterium, a $C_1$-$C_{10}$ alkyl group, a $C_1$-$C_{10}$ alkoxy group, a phenyl group, a biphenyl group, and a terphenyl group;

a $C_1$-$C_{10}$ alkyl group and a $C_1$-$C_{20}$ alkoxy group, each substituted with at least one deuterium; and a phenyl group, a biphenyl group, and a terphenyl group, each substituted with at least one selected from deuterium, a $C_1$-$C_{20}$ alkyl group, a $C_1$-$C_{20}$ alkoxy group, a phenyl group, a biphenyl group, and a terphenyl group.

In various embodiments, $R_1$ to $R_3$, $R_{11}$, and $R_{12}$ may each independently be selected from:

hydrogen, deuterium, a phenyl group, a biphenyl group, and a terphenyl group; and a phenyl group, a biphenyl group, and a terphenyl group, each substituted with at least one selected from deuterium, a phenyl group, a biphenyl group, and a terphenyl group, but embodiments are not limited thereto.

In Formulae 1 and 2A, a1 and a3 each indicate the number of $R_1$ and the number of $R_3$, and may each independently be an integer selected from 0 to 3. When a1 is two or more, two or more groups $R_1$ may be identical to or different from each other, and when a3 is two or more, two or more groups $R_3$ may be identical to or different from each other.

In Formulae 1 and 2B, a2 and a12 each indicate the number of $R_2$ and the number of $R_{12}$, and may each independently be an integer selected from 0 to 4. When a2 is two or more, two or more groups $R_2$ may be identical to or different from each other, and when a12 is two or more, two or more groups $R_{12}$ may be identical to or different from each other.

In Formula 2B, a11 indicates the number of $R_{11}$, and may be an integer selected from 0 to 6. When a11 is two or more, two or more groups $R_{11}$ may be identical to or different from each other.

In various embodiments, a1 to a3, a11, and a12 may each independently be 0, 1, or 2, and for example, may be 0 or 1. However, embodiments are not limited thereto.

In Formula 2A, $R_4$ may be selected from:

a phenyl group, a biphenyl group, and a terphenyl group; and a phenyl group, a biphenyl group, and a terphenyl group, each substituted with at least one selected from deuterium, a $C_1$-$C_{20}$ alkyl group, and a $C_1$-$C_{20}$ alkoxy group.

That is, $R_4$ in Formula 2A does not include an electron-transporting moiety.

In various embodiments, $R_4$ may be selected from groups represented by Formulae 3-1 to 3-7:

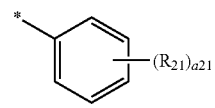

Formula 3-1

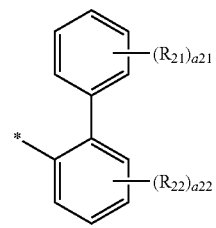

Formula 3-2

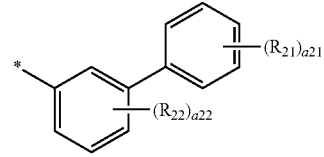

Formula 3-3

-continued

Formula 3-4

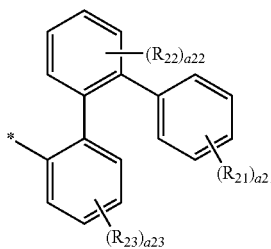

Formula 3-5

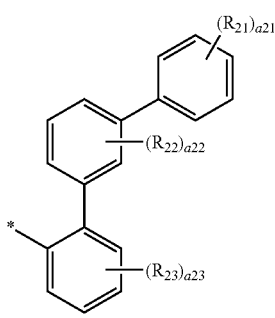

Formula 3-6

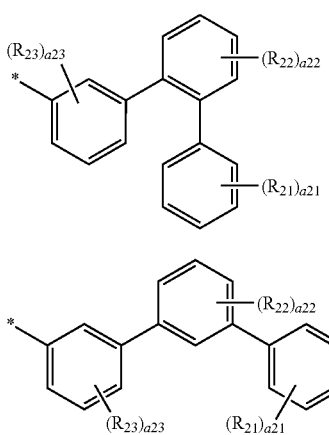

Formula 3-7

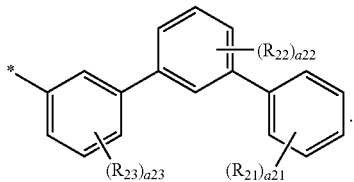

In Formulae 3-1 to 3-7, $R_{21}$ to $R_{23}$ may each independently be hydrogen, deuterium, a $C_1$-$C_{10}$ alkyl group, or a $C_1$-$C_{10}$ alkoxy group, a21 may be an integer selected from 0 to 5, a22 and a23 may each independently be an integer selected from 0 to 4, and

* indicates a binding site to a neighboring atom.

When $R_4$ in Formula 2A is selected from groups represented by Formulae 3-1 to 3-7, the condensed cyclic compound represented by Formula 1 may have a relatively high triplet state $T_1$ energy level.

In Formula 2A, a4 indicates the number of $R_4$, and may be an integer selected from 1 to 4. When a4 is two or more, two or more groups $R_4$ may be identical to or different from each other. Since a4 cannot be 0, Formula 2A has to include at least one $R_4$ as described above.

In various embodiments, a4 may be 1 or 2. However, embodiments are not limited thereto.

In Formula 2A, $R_5$ may be selected from:

hydrogen, deuterium, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one deuterium.

That is, $R_5$ cannot be a ring (i.e., a cyclic group), and in this regard, $R_4$ in Formula 2A may be substituted only at an ortho- or meta-position relative to a carbon atom combined with "N" of a carbazole ring of Formula 1 and $Ar_1$ of Formula 1.

In various embodiments, $R_5$ may be hydrogen, deuterium, a $C_1$-$C_{10}$ alkyl group, or a $C_1$-$C_{10}$ alkoxy group. However, embodiments are not limited thereto.

In Formulae 2A and 2B, * indicates a binding site to a neighboring atom.

The condensed cyclic compound represented by Formula 1 may be represented by one selected from Formulae 1-1 to 1-4:

Formula 1-1

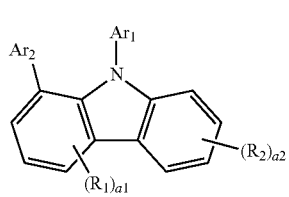

Formula 1-2

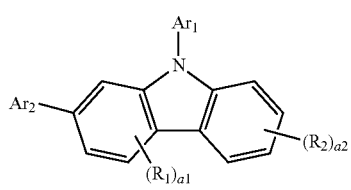

Formula 1-3

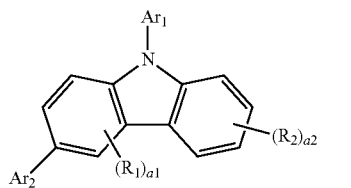

Formula 1-4

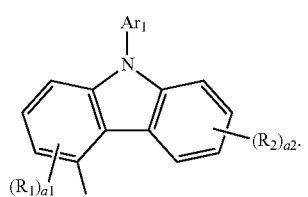

In Formulae 1-1 to 1-4, $Ar_1$, $Ar_2$, $R_1$, $R_2$, a1, and a2 may each independently be the same as described elsewhere herein in connection with those provided in the present specification.

For example, $Ar_1$ in Formulae 1-1 to 1-4 may be one selected from groups represented by Formulae 2A-1 to 2A-5, wherein, in Formulae 2A-1 to 2A-5, $R_3$ and $R_5$ may each independently be the same as described elsewhere herein in connection with those provided in the present specification, a3 may be an integer selected from 0 to 2, and $R_4$, $R_{4a}$, and $R_{4b}$ may each independently be selected from groups represented by Formulae 3-1 to 3-7, but embodiments are not limited thereto.

In various embodiments, $Ar_2$ in Formulae 1-1 to 1-4 may be selected from groups represented by Formulae 2B-1 to 2B-6.

The condensed cyclic compound represented by Formula 1 may be one selected from Compounds 1 to 11, but embodiments are not limited thereto:

1
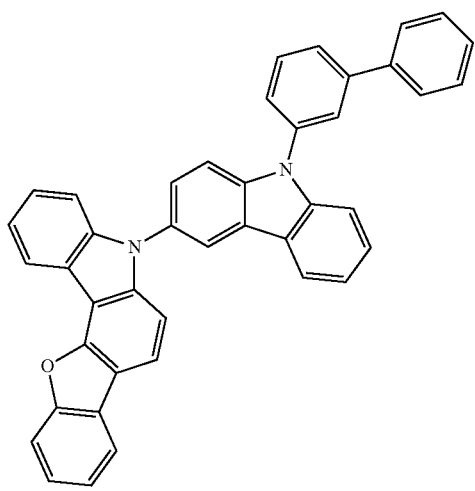
2
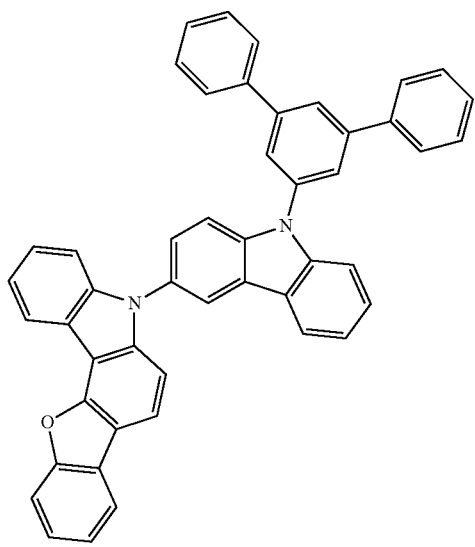
3
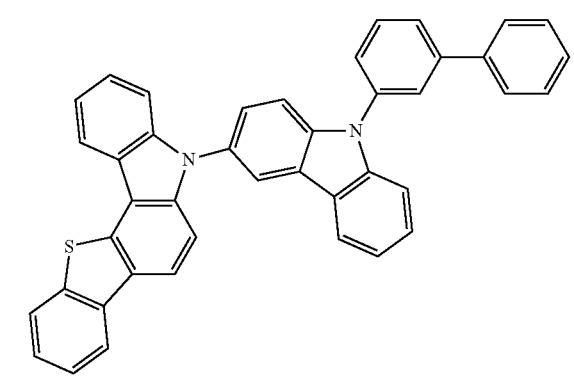
4
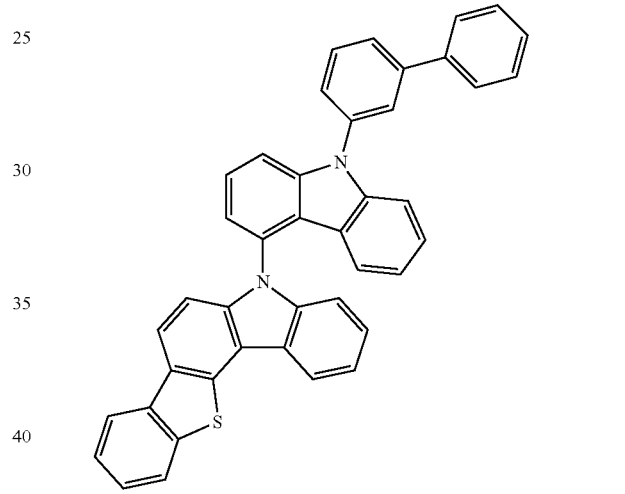
5
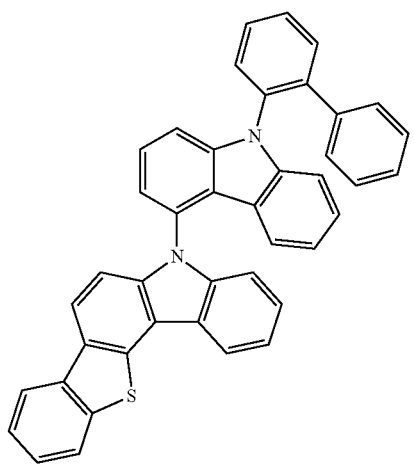
6

7

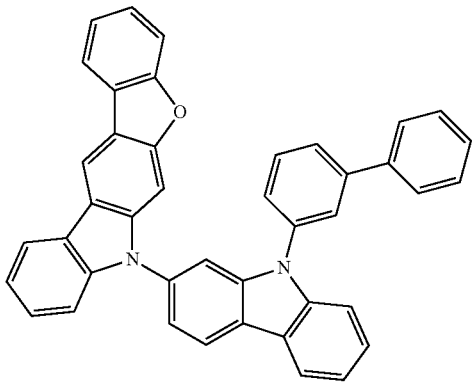

8

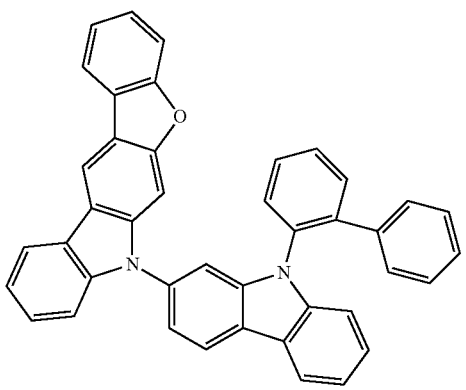

9

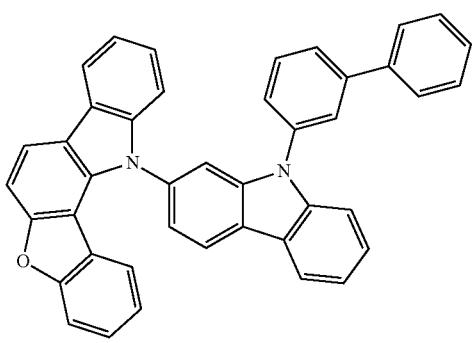

10

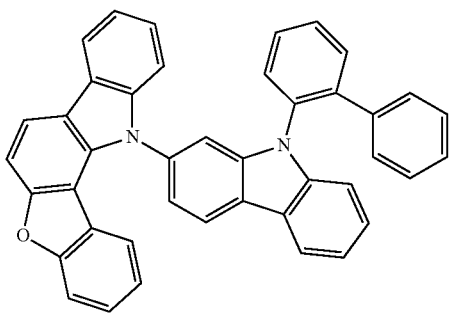

11

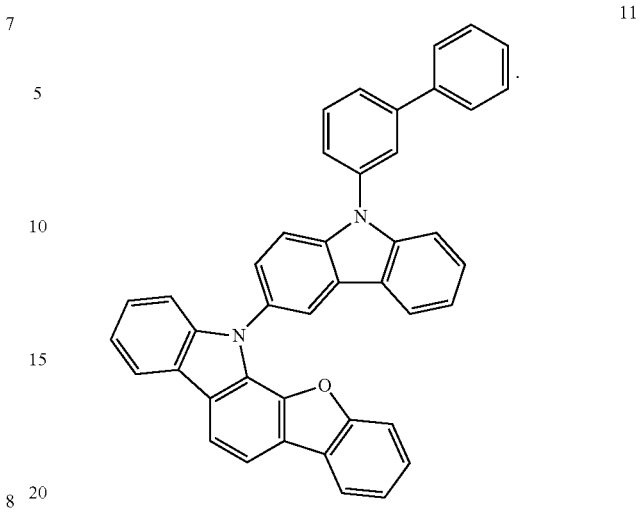

In Formula 1, $Ar_1$ may be a group represented by Formula 2A above. In this regard, the condensed cyclic compound represented by Formula 1 may have a relatively low highest occupied molecular orbital (HOMO) energy level (that is, a relatively large absolute value of a HOMO energy level in a range of, for example, about 5.0 to about 5.3 electron volts (eV), based on simulation data below), and accordingly, may exhibit excellent hole injection and transport characteristics. At the same time, the condensed cyclic compound represented by Formula 1 may have a relatively high triplet state $T_1$ energy level (for example, a triplet state $T_1$ energy level of 2.95 eV or more, based on simulation data below). Thus, when an electronic device, such as an organic light-emitting device, includes the condensed cyclic compound represented by Formula 1, the condensed cyclic compound represented by Formula 1 may contribute to implementing high luminous efficiency and long lifespan.

In addition, $Ar_2$ in Formula 1 may be a group represented by Formula 2B above. Since ring $A_1$ in Formula 2B is "a dibenzofuran ring or a dibenzothiophene ring", the condensed cyclic compound represented by Formula 1 may have a relatively high triplet state $T_1$ energy level. Thus, when an electronic device, such as an organic light-emitting device, includes the condensed cyclic compound represented by Formula 1, the organic light-emitting device may have high luminous efficiency and long lifespan.

HOMO, LUMO, triplet state $T_1$, and singlet state $S_1$ energy levels of Compounds 1, 2, 3, 4, 9, and 11 and Compounds D, E and F are calculated by Density Function Theory (DFT) methods of Gaussian programs in which molecular structures are optimized at the B3LYP/6-31G(d,p) levels, and the results are shown in Table 1.

TABLE 1

| Compound No. | HOMO (eV) | LUMO (eV) | $T_1$ (eV) | $S_1$ (eV) |
| --- | --- | --- | --- | --- |
| 1  | −5.063 | −1.106 | 3.005 | 3.544 |
| 2  | −5.124 | −1.087 | 2.990 | 3.581 |
| 3  | −5.071 | −1.241 | 3.005 | 3.498 |
| 4  | −5.114 | −1.139 | 2.974 | 3.565 |
| 9  | −5.258 | −1.057 | 2.976 | 3.651 |
| 11 | −5.141 | −1.077 | 2.969 | 3.669 |
| D  | −5.155 | −2.037 | 2.707 | 2.77  |
| E  | −4.961 | −1.12  | 2.907 | 3.47  |
| F  | −4.972 | −1.217 | 2.925 | 3.407 |

TABLE 1-continued
| Compound No. | HOMO (eV) | LUMO (eV) | T₁ (eV) | S₁ (eV) |
|---|---|---|---|---|
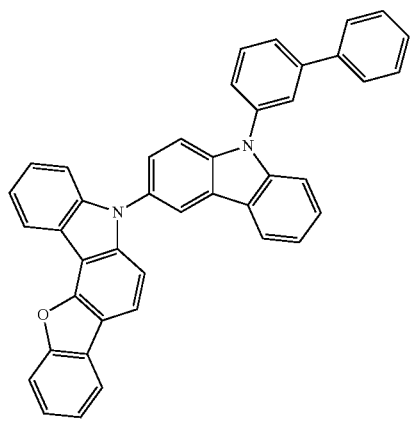
1
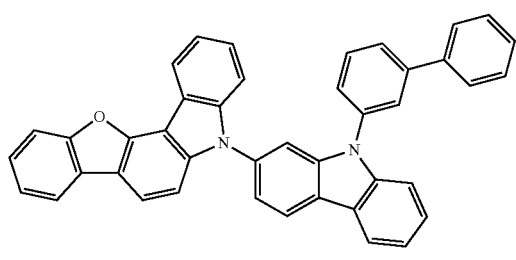
2
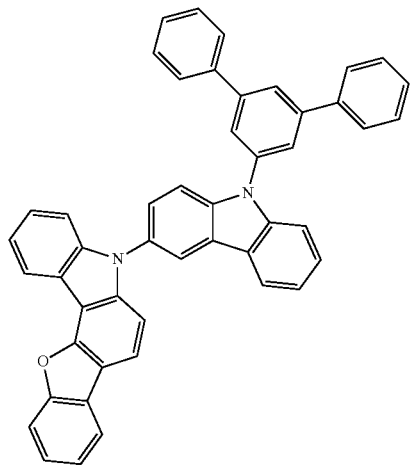
3
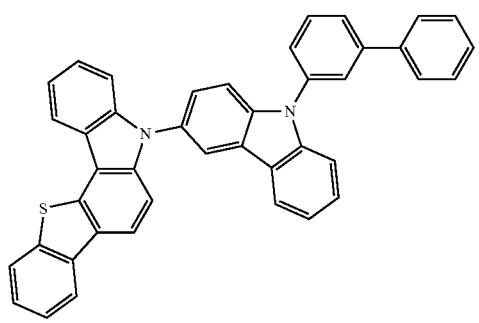
4
TABLE 1-continued
| Compound No. | HOMO (eV) | LUMO (eV) | T₁ (eV) | S₁ (eV) |
|---|---|---|---|---|
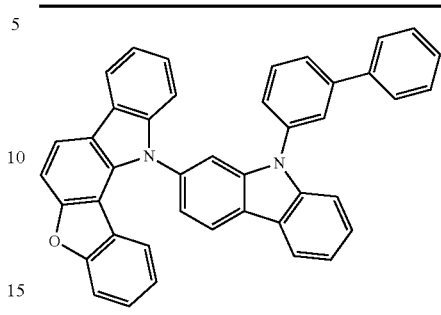
9
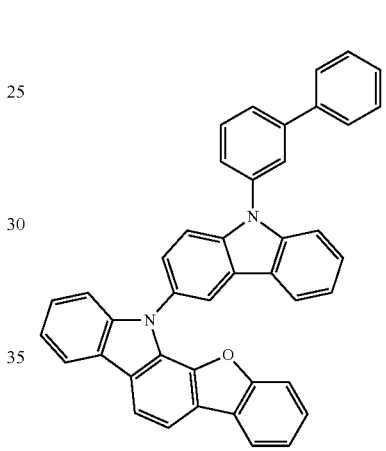
11
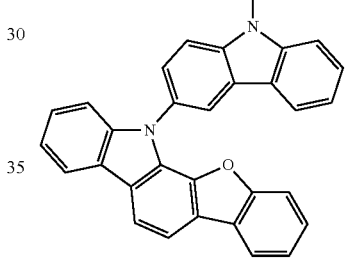
D TABLE 1-continued

| Compound No. | HOMO (eV) | LUMO (eV) | $T_1$ (eV) | $S_1$ (eV) |
| --- | --- | --- | --- | --- |

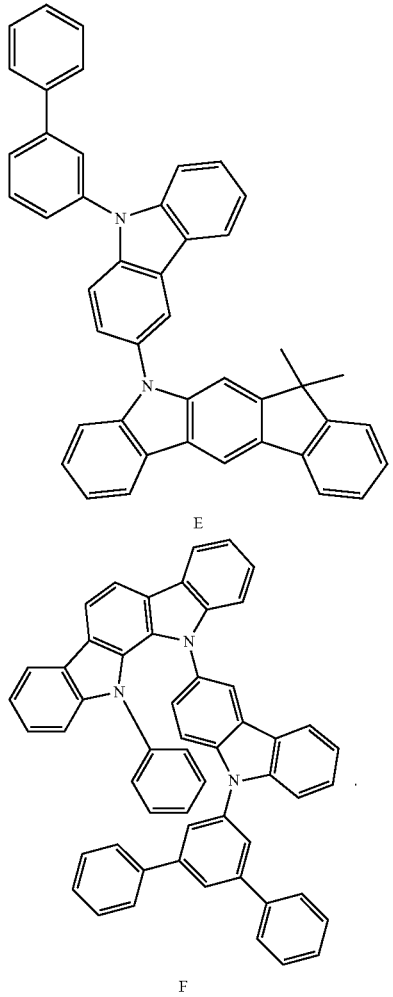

E

F

According to Table 1, it is confirmed that Compounds 1, 2, 3, 4, 9, and 11 have relatively low HOMO levels and relatively high triplet state $T_1$ energy levels at the same time.

Synthesis methods of the condensed cyclic compound represented by Formula 1 may be understood by those of ordinary skill in the art by referring to Synthesis Examples that will described below.

Therefore, the condensed cyclic compound represented by Formula 1 may be suitable for use in an organic layer of an organic light-emitting device, and for example, may be suitable for use as a host or a material for forming a hole transport region in an emission layer in an organic layer.

In this regard, according to another aspect of the present inventive concept, there is provided an organic light-emitting device including:
a first electrode;
a second electrode; and
an organic layer disposed between the first electrode and the second electrode,
wherein the organic layer includes an emission layer and at least one condensed cyclic compound represented by Formula 1.

The organic light-emitting device may include the condensed cyclic compound represented by Formula 1 in the organic layer, thereby exhibiting low driving voltage, high luminous efficiency, high power efficiency, high quantum emission efficiency, and long lifespan.

The condensed cyclic compound represented by Formula 1 may be used between a pair of electrodes in the organic light-emitting device. For example, at least one selected from the emission layer, a hole transport region between the first electrode and the emission layer (for example, the hole transport region including a hole injection layer, a hole transport layer, an electron blocking layer, or a combination thereof), and an electron transport region between the emission layer and the second electrode (for example, the electron transport region including a hole blocking layer, an electron transport layer, an electron injection layer, or a combination thereof) may include the condensed cyclic compound represented by Formula 1.

For example, the emission layer may include the condensed cyclic compound represented by Formula 1. Here, the condensed cyclic compound represented by Formula 1 in the emission layer may serve as a host, and the emission layer may further include a dopant (for example, a fluorescent dopant or a phosphorescent dopant). The emission layer may be a green emission layer emitting green light or a blue emission layer emitting blue light.

In various embodiments, the emission layer may include the condensed cyclic compound represented by Formula 1, and the emission layer may further include a phosphorescent dopant, wherein the emission layer may emit blue light.

In various embodiments, the emission layer may include a host and a dopant, wherein the host may include the condensed cyclic compound represented by Formula 1. Here, an amount of the host may be greater than that of the dopant.

In various embodiments, the hole transport region may include the condensed cyclic compound represented by Formula 1.

In various embodiments, the hole transport region may include a hole transport layer, and the hole transport layer may include the condensed cyclic compound represented by Formula 1.

In various embodiments, the hole transport region may include a hole transport layer and an electron blocking layer, and the electron blocking layer may be disposed between the hole transport layer and the emission layer and may include the condensed cyclic compound represented by Formula 1.

In various embodiments, the hole transport region may include a hole transport layer and an electron blocking layer, wherein the electron blocking layer may be disposed between the hole transport layer and the emission layer, and the electron blocking layer and the emission layer may each include the condensed cyclic compound represented by Formula 1. Here, the condensed cyclic compound represented by Formula 1 in the electron blocking layer may be identical to or different from the condensed cyclic compound represented by Formula 1 in the emission layer.

The expression that "(an organic layer) includes at least one condensed cyclic compound" as used herein may include an embodiment in which "(an organic layer) includes identical condensed cyclic compounds represented by Formula 1" and an embodiment in which (an organic layer) includes two or more different condensed cyclic compounds represented by Formula 1".

For example, the organic layer may include, as the condensed cyclic compound represented by Formula 1, only Compound 1. Here, Compound 1 may be included in the emission layer of the organic light-emitting device. In various embodiments, the organic layer may include, as the condensed cyclic compound represented by Formula 1, Compound 1 and Compound 2. Here, Compound 1 and Compound 2 may be included in an identical layer (for example, Compound 1 and Compound 2 may both be included in the emission layer), or in different layers (for example, Compound 1 may be included in the emission layer and Compound 2 may be included in the electron blocking layer).

The first electrode may be an anode, which is a hole injection electrode, and the second electrode may be a cathode, which is an electron injection electrode. In various embodiments, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" as used herein may refer to a single layer and/or a plurality of layers disposed between the first electrode and the second electrode of the organic light-emitting device. The "organic layer" may include not only an organic compound, but also a metal-containing organometallic complex.

FIG. 1 is a schematic cross-sectional view of an organic light-emitting device 10 according to an embodiment. Hereinafter, the structure of an organic light-emitting device according to an embodiment and a method of manufacturing an organic light-emitting device, according to an embodiment, will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be, for example, formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), and zinc oxide (ZnO). In various embodiments, metals, such as magnesium (Mg), aluminum (Al), aluminum-lithium (Al—Li), calcium (Ca), magnesium-indium (Mg—In), and magnesium-silver (Mg—Ag), may be used as the material for forming the first electrode 11.

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer; and an electron transport region.

The hole transport region may be disposed between the first electrode 11 and the emission layer.

The hole transport region may include a hole injection layer, a hole transport layer, an electron blocking layer, a buffer layer, or a combination thereof.

The hole transport region may include only either a hole injection layer or a hole transport layer. In various embodiments, the hole transport region may have a structure of hole injection layer/hole transport layer, a structure of hole injection layer/hole transport layer/electron blocking layer, or a structure of hole transport layer/electron blocking layer, wherein the layers of each structure are sequentially stacked from the first electrode 11 in the stated order.

When hole transport region includes a hole injection layer, the hole injection layer may be formed on the first electrode 11 by using one or more suitable methods selected from vacuum deposition, spin coating, casting, and Langmuir-Blodgett (LB) deposition.

When the hole injection layer is formed using vacuum deposition, the deposition conditions may vary depending on a material that is used to form the hole injection layer to be deposited, and the structure and thermal characteristics of the hole injection layer to be formed. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec, but the deposition conditions are not limited thereto.

When the hole injection layer is formed using spin coating, the coating conditions may vary depending on a material that is used to form the hole injection layer to be deposited, and the structure and thermal characteristics of the hole injection layer to be formed. For example, a coating speed may be from about 2,000 revolutions per minute (rpm) to about 5,000 rpm and a temperature at which a heat treatment is performed to remove a solvent after coating may be from about 80° C. to about 200° C., but the coating conditions are not limited thereto.

Conditions for forming a hole transport layer and an electron blocking layer may be understood by referring to conditions for forming the hole injection layer.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly (4-styrene sulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

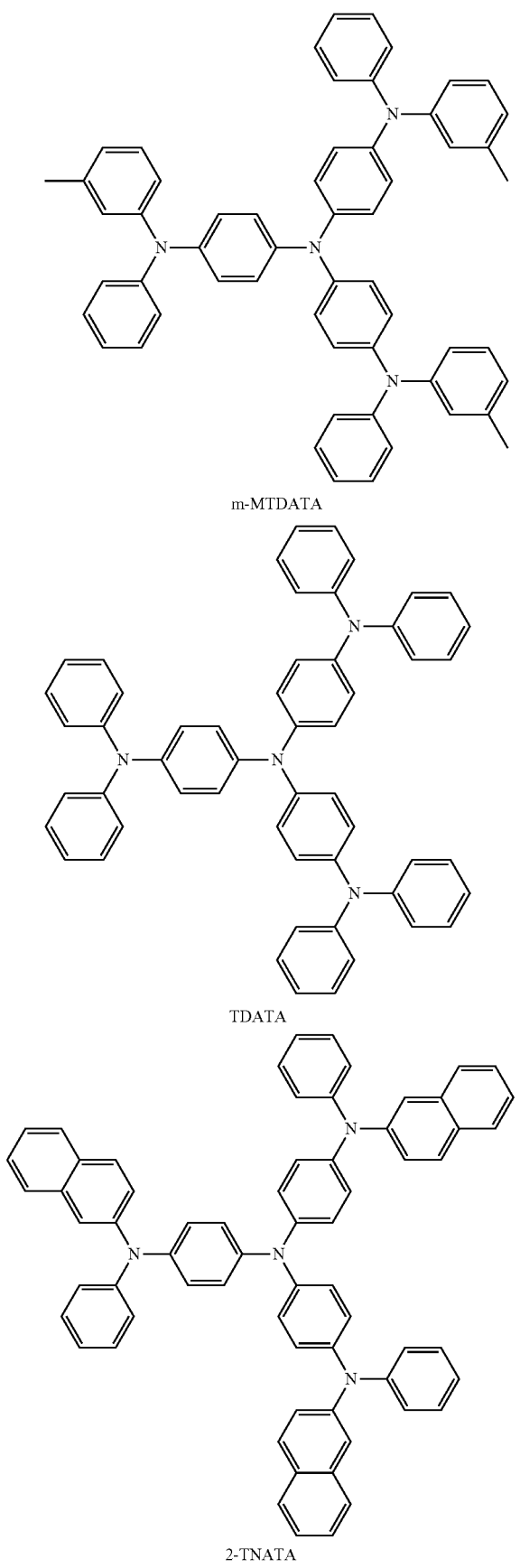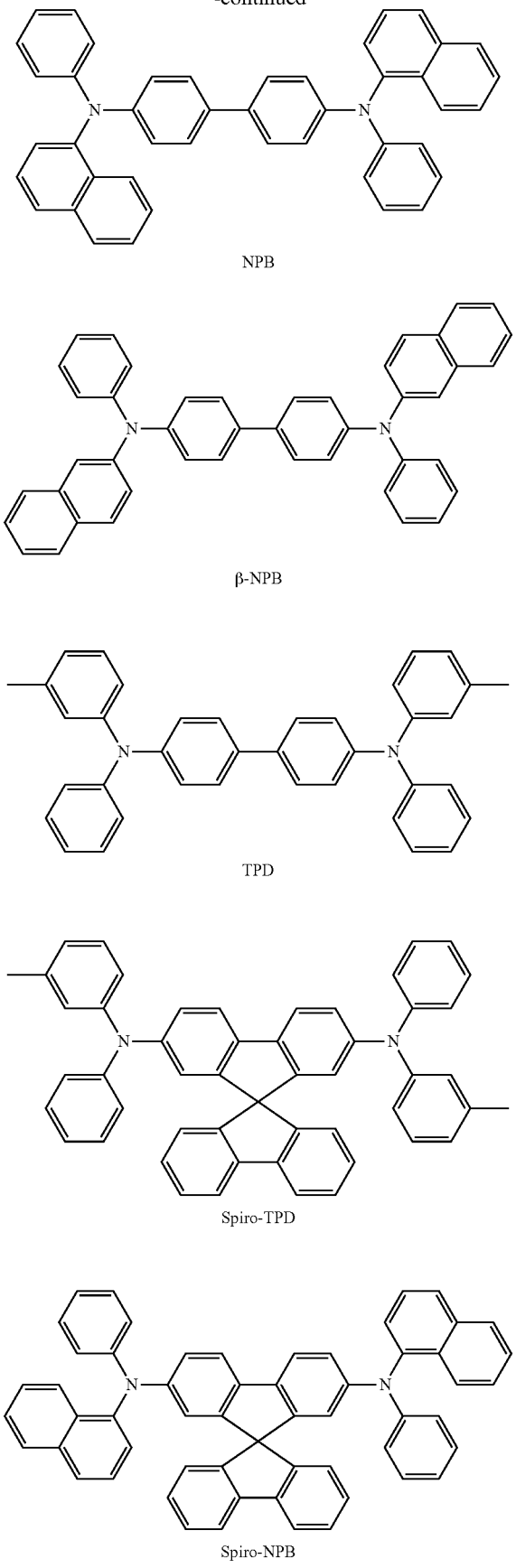

-continued

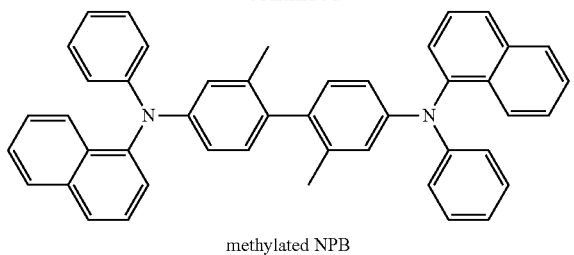

methylated NPB

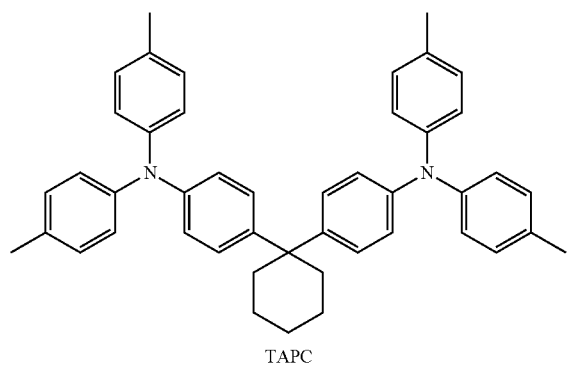

TAPC

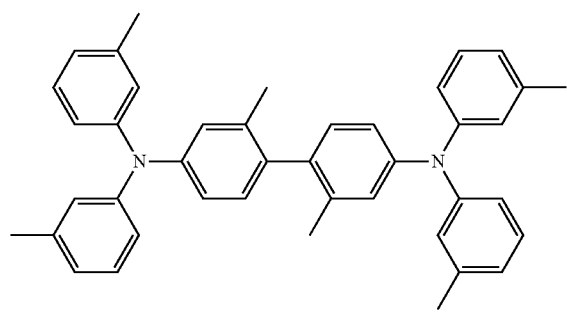

HMTPD

Formula 201

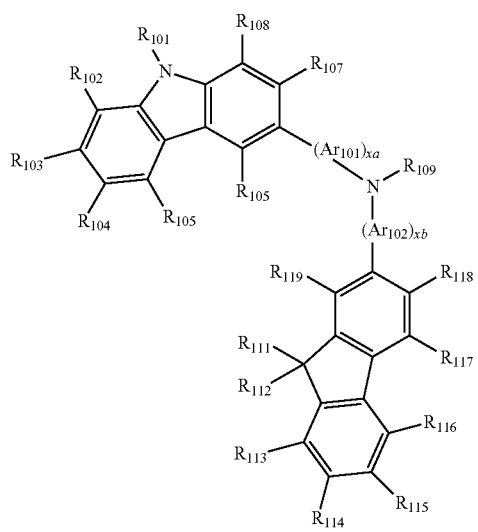

Formula 202

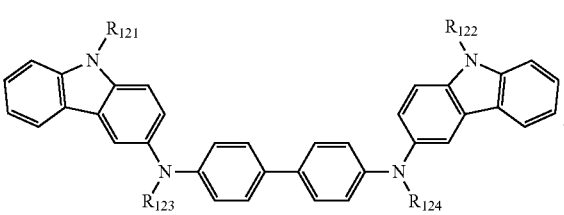

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or may be 0, 1, or 2. For example, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group) and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from:
a phenyl group, a naphthyl group, an anthracenyl group, and a pyridinyl group; and
a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In various embodiments, the compound represented by Formula 201 may be represented by Formula 201A, but embodiments are not limited thereto:

Formula 201A

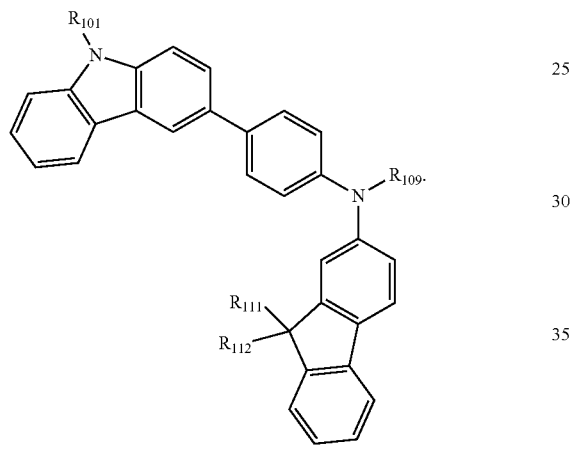

In Formula 201A, $R_{101}$, $R_{111}$, $R_{112}$, and $R_{109}$ may each independently be the same as described elsewhere herein in connection with those provided in the present specification.

For example, the compound represented by Formula 201 and the compound represented by Formula 202 may each independently include any of Compounds HT1 to HT20, but embodiments are not limited thereto:

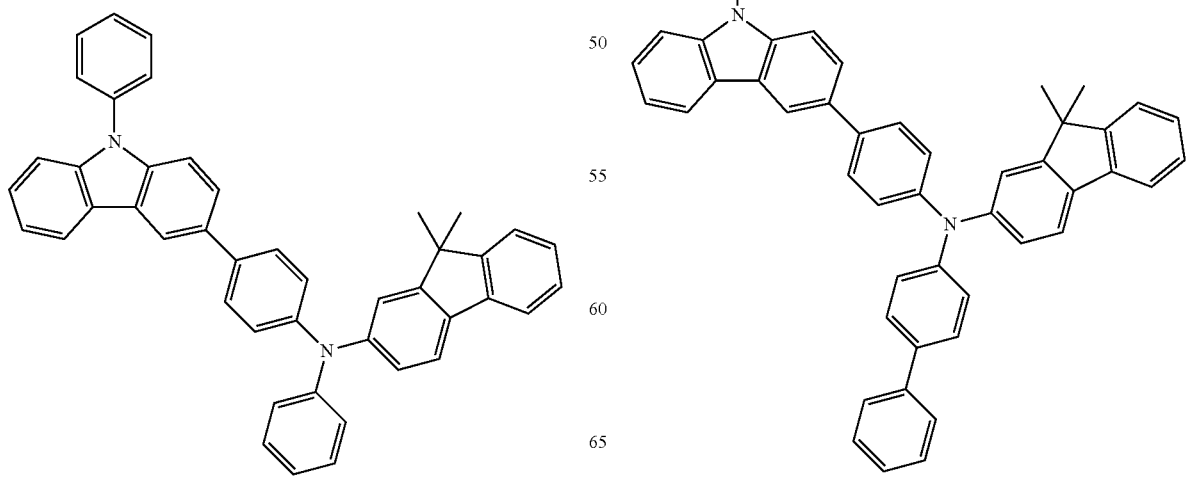

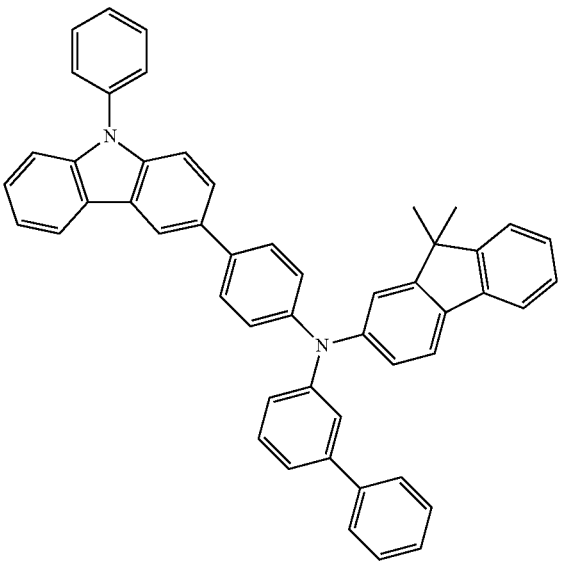

HT4
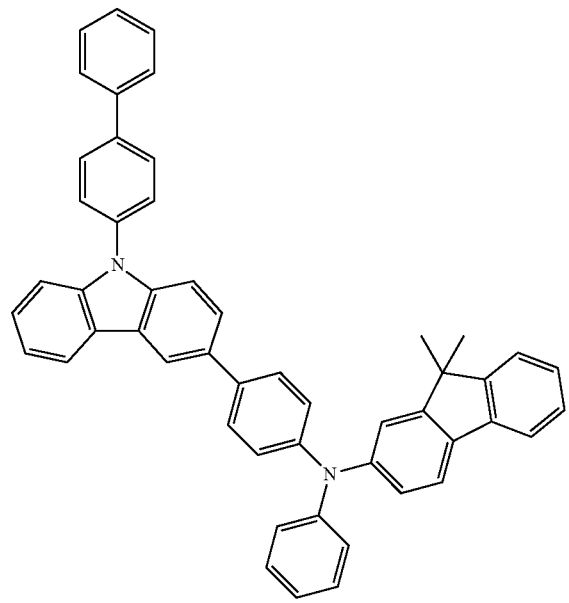
HT6
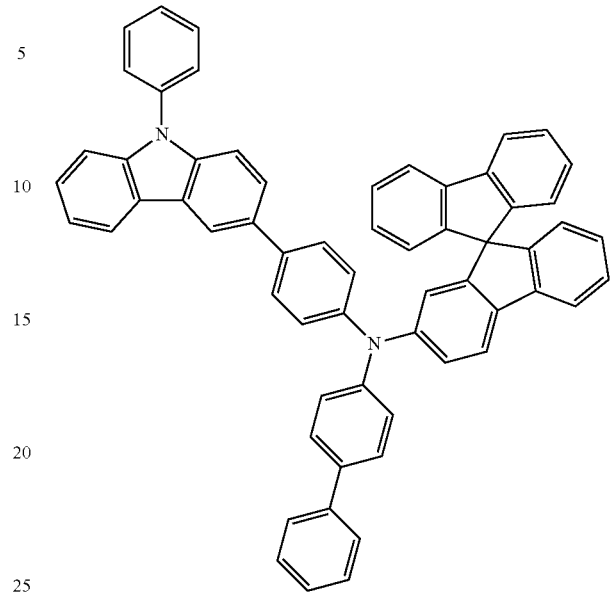
HT5
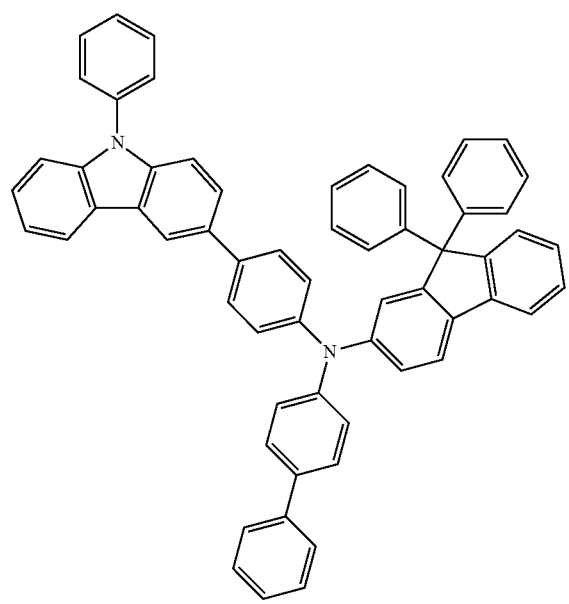
HT7
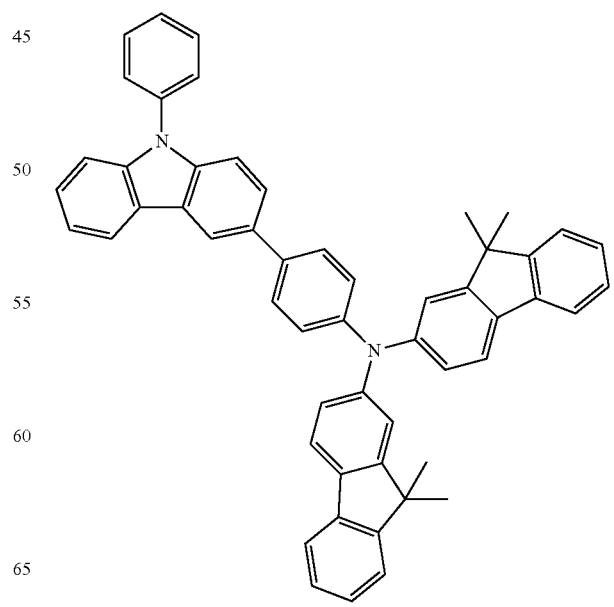

HT8
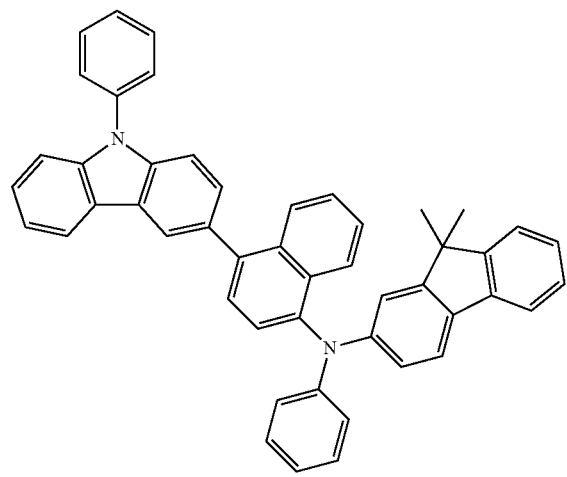
HT11
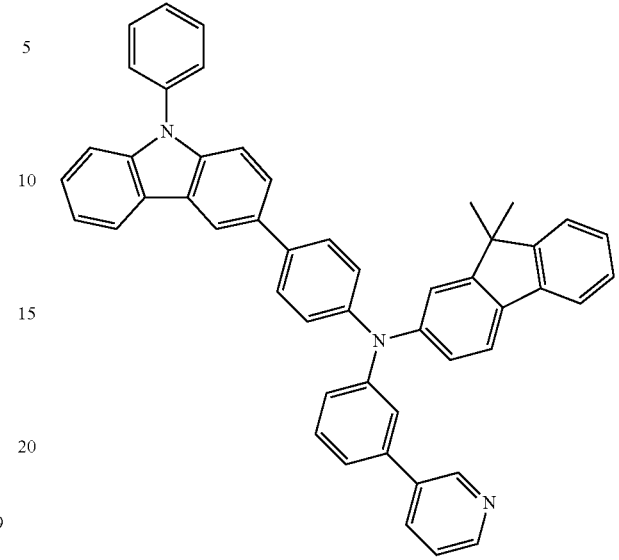
HT9
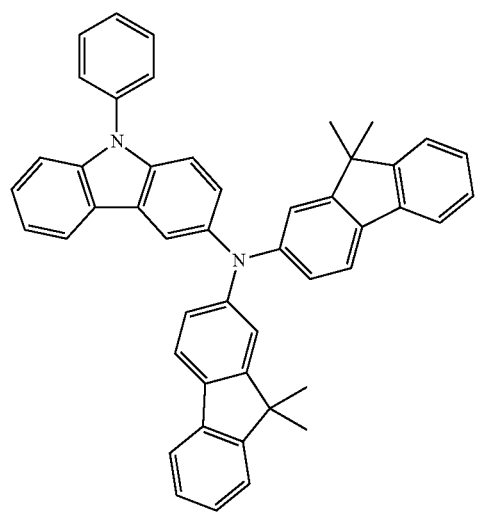
HT12
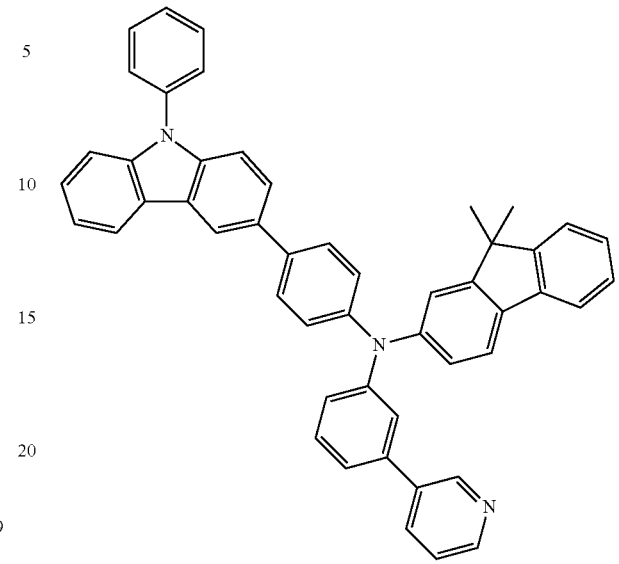
HT10
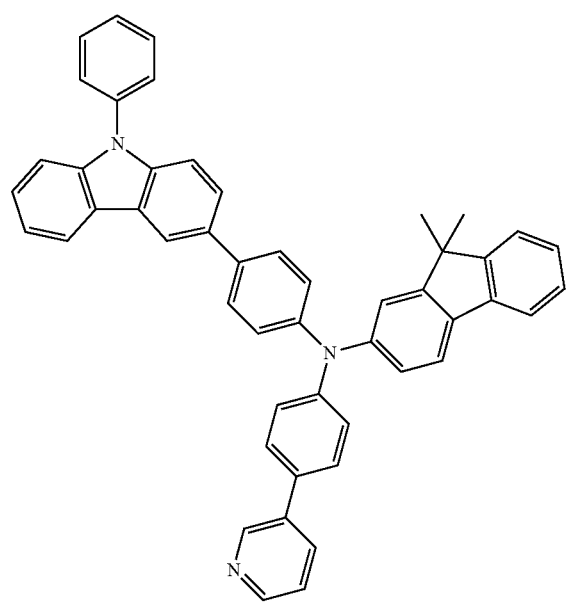
HT13
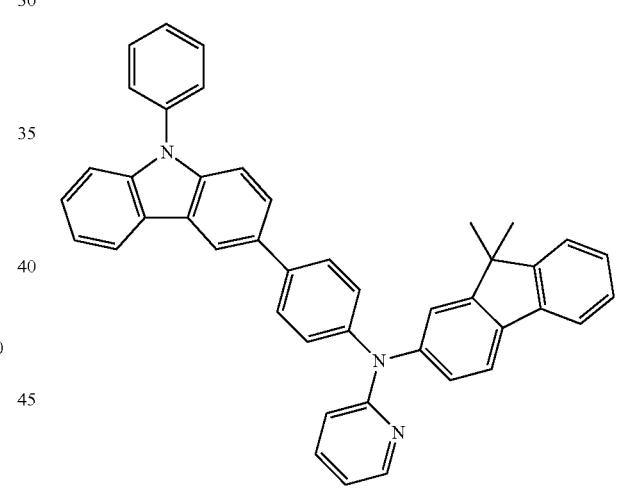

-continued

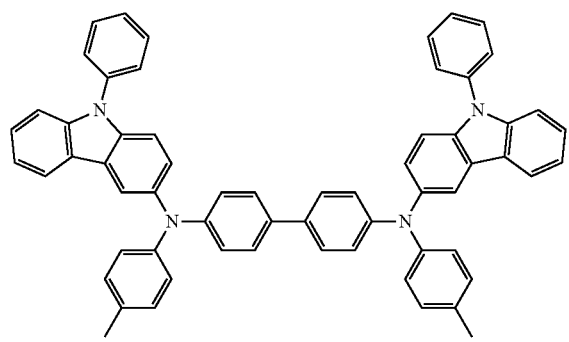
HT14

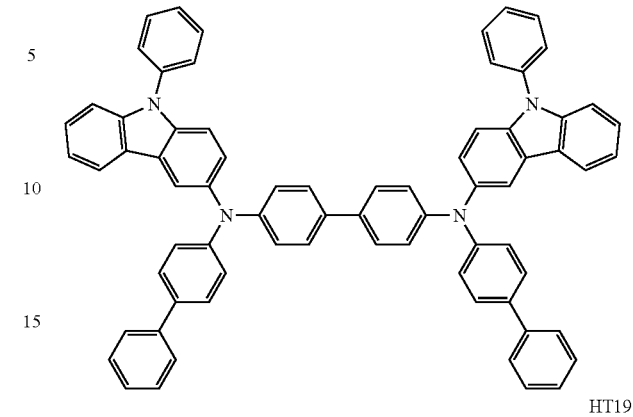
HT18

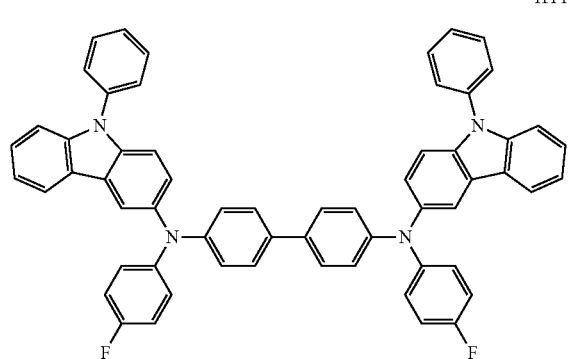
HT15

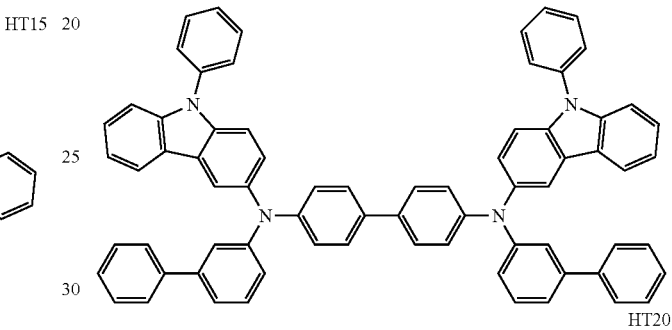
HT19

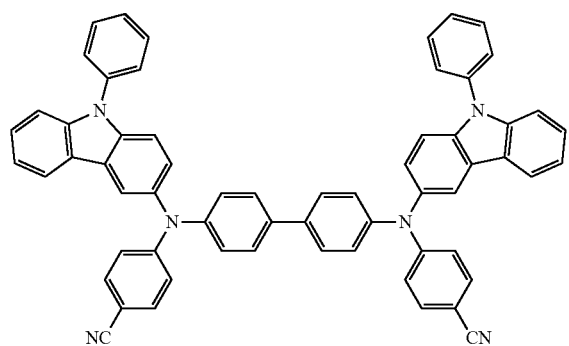
HT16

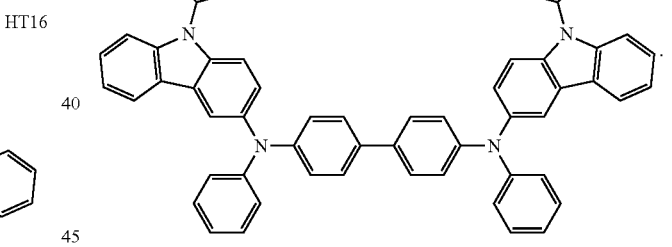
HT20

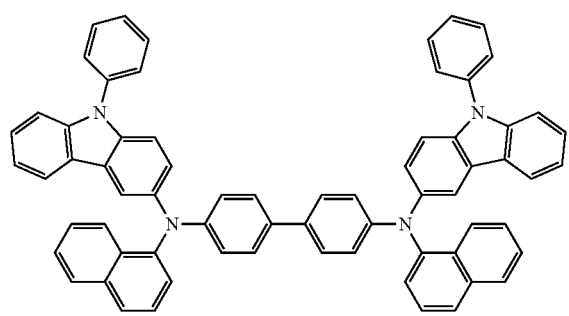
HT17

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) and 2,3,5,6-tetrafluoro-tetracyano-1,4-benzoquinonedimethane (F4-TCNQ); a metal oxide, such as a tungsten oxide and a molybdenum oxide; and a cyano group-containing compound, such as Compounds HT-D1 and HP-1, but embodiments are not limited thereto.

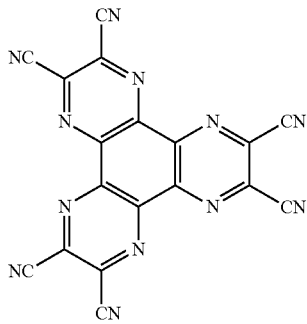

Compound HT-D1

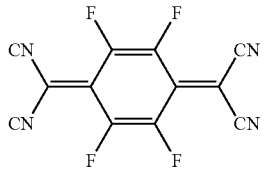

F4-TCNQ

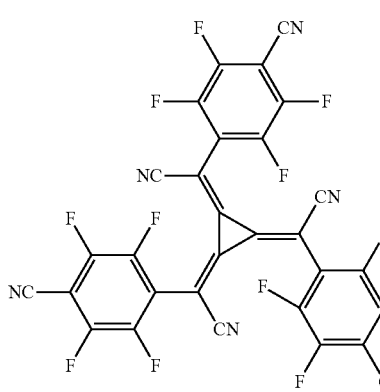

HP-1

The hole transport region may further include a buffer layer.

The buffer layer may compensate for an optical resonance distance according to a wavelength of light emitted from the emission layer, and thus, the efficiency of a formed organic light-emitting device may be improved.

The emission layer may be formed on the hole transport region by using one or more suitable methods selected from vacuum deposition, spin coating, casting, and LB deposition. When the emission layer is formed using vacuum deposition and spin coating, the deposition and coating conditions for the emission layer may be similar with those for forming the hole injection layer, although deposition and coating conditions may vary depending on a material that is used to form the emission layer.

The hole transport region may further include an electron blocking layer. The electron blocking layer may include a known compound, such as mCP, but embodiments are not limited thereto:

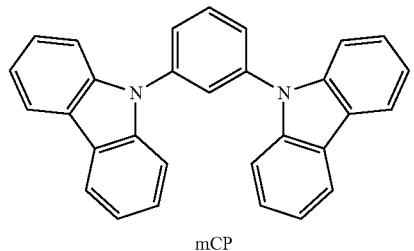

mCP

In various embodiments, the electron blocking layer may include the condensed cyclic compound represented by Formula 1, but embodiments are not limited thereto.

When the organic light-emitting device 10 is a full color organic light-emitting device, the emission layer may be patterned into a red emission layer, a green emission layer, and a blue emission layer. In various embodiments, the emission layer may have a stacked structure including a red emission layer, a green emission layer and/or a blue emission layer, thereby emitting light.

The emission layer may include the condensed cyclic compound represented by Formula 1. The emission layer may further include a dopant, wherein the dopant may include at least one of a phosphorescent dopant and a fluorescent dopant.

For example, a host in the emission layer may include the condensed cyclic compound represented by Formula 1.

A dopant in the emission layer may be a fluorescent dopant that emits light according to a fluorescent emission mechanism, or a phosphorescent dopant that emits light according to a phosphorescent emission mechanism.

In various embodiments, a dopant in the emission layer may be a phosphorescent dopant, wherein the phosphorescent dopant may include an organometallic compound represented by Formula 81:

$$M(L_{81})_{n81}(L_{82})_{n82} \quad \text{Formula 81}$$

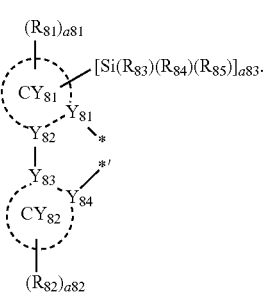

Formula 81A

In Formulae 81 and 81A,

M may be selected from iridium (Ir), platinum (Pt), osmium (Os), titanium (Ti), zirconium (Zr), hafnium (Hf), europium (Eu), terbium (Tb), thulium (Tm), and rhodium (Rh), $L_{81}$ may be a ligand represented by Formula 81A, and n81 may be an integer selected from 1 to 3, wherein, when n81 is two or more, two or more groups $L_{81}$ may be identical to or different from each other, $L_{82}$ may be an organic ligand, and n82 may be an integer selected from 0 to 4, wherein, when n82 is two or more, two or more groups $L_{82}$ may be identical to or different from each other, $Y_{81}$ to $Y_{84}$ may each independently be C or N, $Y_{81}$ and $Y_{82}$ may be linked via a single bond or a double bond, and $Y_{83}$ and $Y_{84}$ may be linked via a single bond or a double bond, $CY_{81}$ and $CY_{82}$ may each independently be selected from a $C_5$-$C_{30}$ carbocyclic group and a $C_1$-$C_{30}$ heterocarbocyclic group, $CY_{81}$ and $CY_{82}$ may be further optionally linked to each other via an organic linking group, $R_{81}$ to $R_{85}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{81}$)(Q$_{82}$)(Q$_{83}$), —N(Q$_{84}$)(Q$_{85}$), —B(Q$_{86}$)(Q$_{87}$), and —P(=O)(Q$_{88}$)(Q$_{89}$), a81 to a83 may each independently be an integer selected from 0 to 5, wherein, when a81 is two or more, two or more groups $R_{81}$ may be identical to or different from each other, when a82 is two or more, two or more groups $R_{82}$ may be identical to or different from each other, when a81 is two or more, two or more neighboring groups $R_{81}$ may be linked to form a saturated or unsaturated ring, when a82 is two or more, two or more neighboring groups $R_{82}$ may be linked to form a saturated or unsaturated ring,

* and *' in Formula 81A each independently indicate a binding site to M of Formula 81, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{91}$)(Q$_{92}$)(Q$_{93}$), and Q$_{81}$ to Q$_{89}$ and Q$_{91}$ to Q$_{93}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In various embodiments, in Formula 81A, a83 may be 1 or 2, $R_{83}$ to $R_{85}$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but embodiments are not limited thereto.

In various embodiments, in Formula 81A, $Y_{81}$ may be N, $Y_{82}$ and $Y_{83}$ may each independently be C, and $Y_{84}$ may be N or C, and $CY_{81}$ and $CY_{82}$ may each independently be selected from a cyclopentadiene group, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a corozene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilol group, and a 2,3-dihydro-1H-imidazole group.

In various embodiments, in Formula 81A, $Y_{81}$ may be N, $Y_{82}$ to $Y_{84}$ may each independently be C, $CY_{81}$ may be selected from a 5-membered ring including, as a ring-forming atom, two N atoms, and $CY_{82}$ may be selected from a benzene group, a naphthalene group, a fluorene group, a dibenzofuran group, and a dibenzothiophene group, but embodiments are not limited thereto.

In various embodiments, in Formula 81A, $Y_{81}$ may be N, $Y_{82}$ to $Y_{84}$ may each independently be C, $CY_{81}$ may be an imidazole group or a 2,3-dihydro-1H-imidazole group, and $CY_{82}$ may be selected from a benzene group, a naphthalene group, a fluorene group, a dibenzofuran group, and a dibenzothiophene group, but embodiments are not limited thereto.

In various embodiments, in Formula 81A, $Y_{81}$ may be N, $Y_{82}$ to $Y_{84}$ may each independently be C, $CY_{81}$ may be selected from a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an isobenzothiazole group, a benzoxazole group, and an isobenzoxazole group, and $CY_{82}$ may be selected from a cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group, and a dibenzosilol group.

In various embodiments, in Formula 81A, $R_{81}$ and $R_{82}$ may each independently be selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$B(Q_{86})(Q_{87})$, and —$P(=O)(Q_{88})(Q_{89})$, and $Q_{86}$ to $Q_{89}$ may each independently be selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In various embodiments, in Formula 81A, $R_{81}$ and $R_{82}$ may each independently be selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —B(Q$_{86}$)(Q$_{87}$) and —P(=O)(Q$_{88}$)(Q$_{89}$), and Q$_{86}$ to Q$_{89}$ may each independently be selected from: —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In various embodiments, in Formula 81A, $R_{81}$ and $R_{82}$ may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, but embodiments are not limited thereto:

Formula 9-1

Formula 9-2

Formula 9-3

Formula 9-4

Formula 9-5

Formula 9-6

Formula 9-7

Formula 9-8

Formula 9-9

Formula 9-10

Formula 9-11

Formula 9-12

Formula 9-13

Formula 9-14

Formula 9-15

Formula 9-16

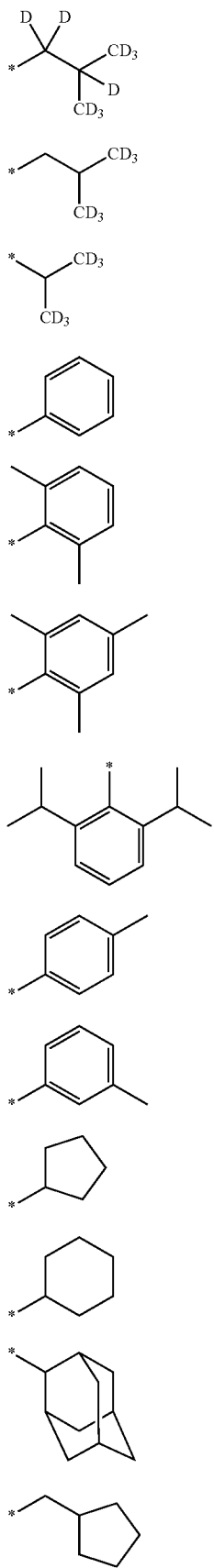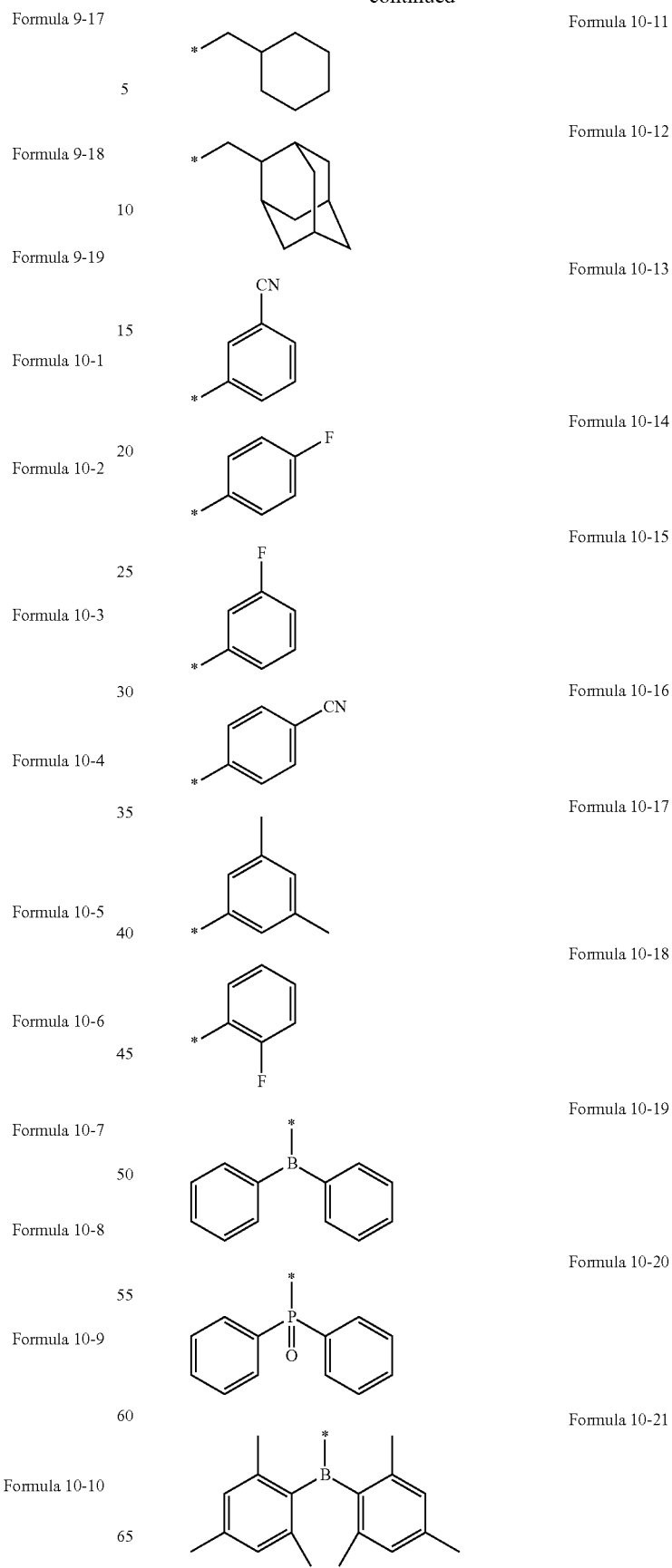

-continued

Formula 10-22
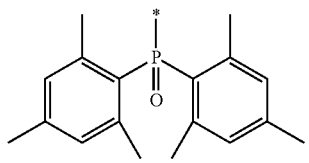

Formula 10-23
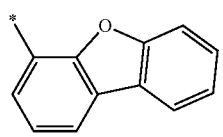

Formula 10-24
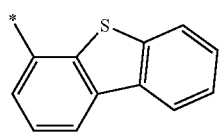

Formula 10-25
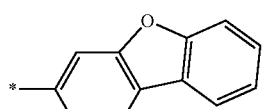

Formula 10-26
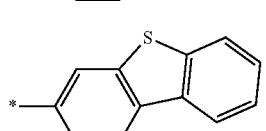

Formula 10-27
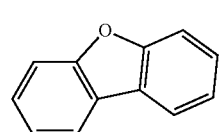

Formula 10-28
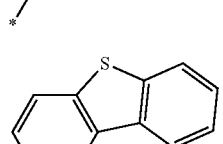

Formula 10-29
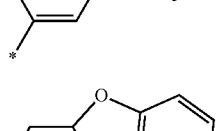

Formula 10-30
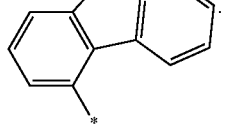

In Formulae 9-1 to 9-19 and 10-1 to 10-30, * indicates a binding site to a neighboring atom.

In various embodiments, in Formula 81A, the sum of a81 and a82 may be 1 or greater, wherein at least one selected from $R_{81}$ in the number of a81 and $R_{82}$ in the number of a82 may be a cyano group.

In various embodiments, in Formula 81A, a82 may be one or more, wherein at least one selected from $R_{82}$ in the number of a82 may be a cyano group.

In various embodiments, in Formula 81A, at least one selected from $R_{81}$ in the number of a81 and $R_{82}$ in the number of a82 may be deuterium. In various embodiments, in Formula 81, $L_{82}$ may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

Formula 3-1(1)
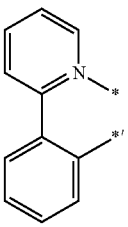

Formula 3-1(2)
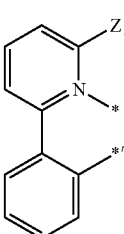

Formula 3-1(3)
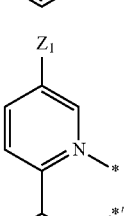

Formula 3-1(4)
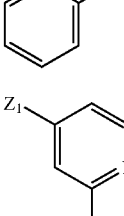

Formula 3-1(5)
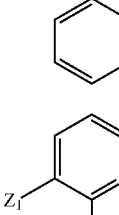

Formula 3-1(6)
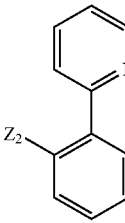

-continued
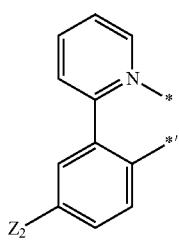
Formula 3-1(7)
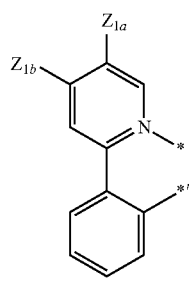
Formula 3-1(13)
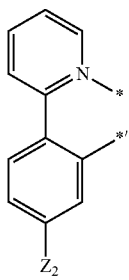
Formula 3-1(8)
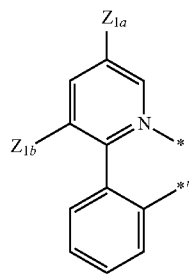
Formula 3-1(14)
Formula 3-1(9)
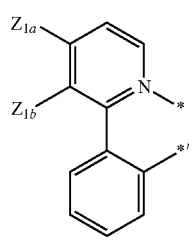
Formula 3-1(15)
Formula 3-1(10)
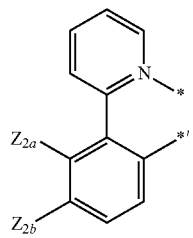
Formula 3-1(16)
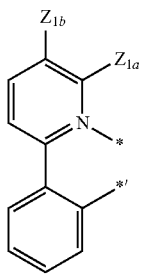
Formula 3-1(11)
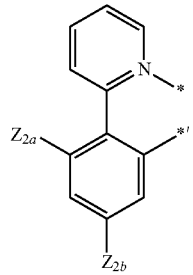
Formula 3-1(17)
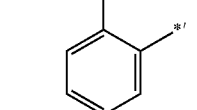
Formula 3-1(12)
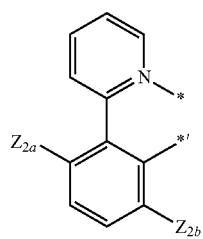
Formula 3-1(18)

Formula 3-1(19)
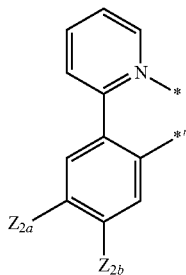
Formula 3-1(20)
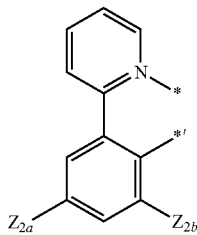
Formula 3-1(21)
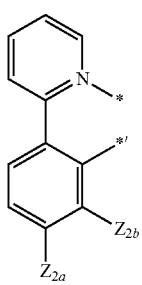
Formula 3-1(22)
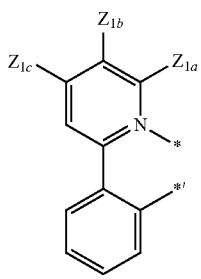
Formula 3-1(23)
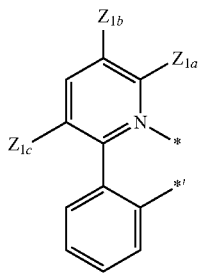
Formula 3-1(24)
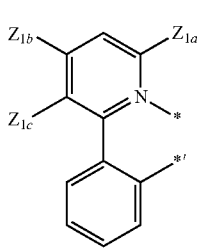
Formula 3-1(25)
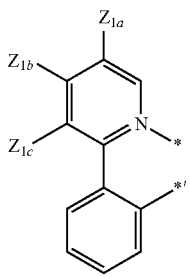
Formula 3-1(26)
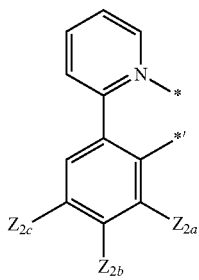
Formula 3-1(27)
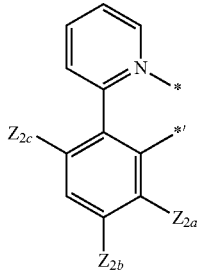
Formula 3-1(28)
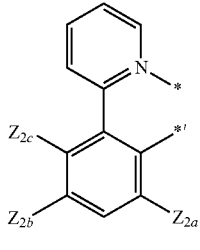
Formula 3-1(29)
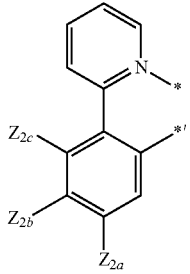

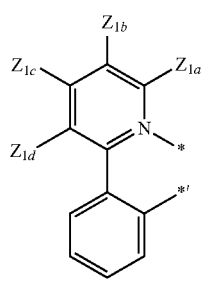
Formula 3-1(30)
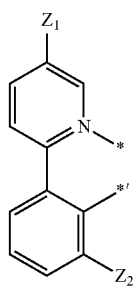
Formula 3-1(36)
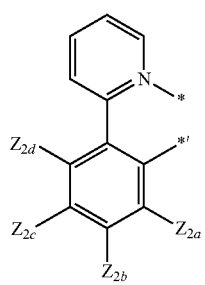
Formula 3-1(31)
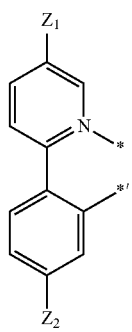
Formula 3-1(37)
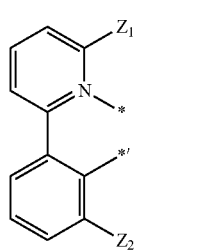
Formula 3-1(32)
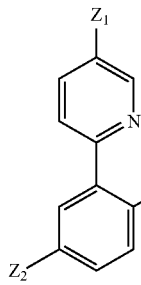
Formula 3-1(38)
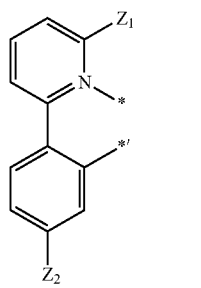
Formula 3-1(33)
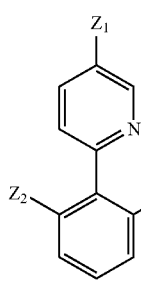
Formula 3-1(39)
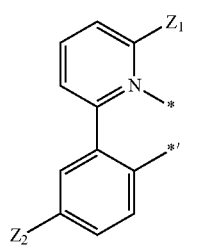
Formula 3-1(34)
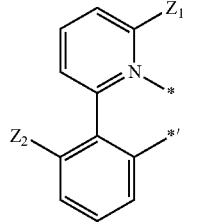
Formula 3-1(35)
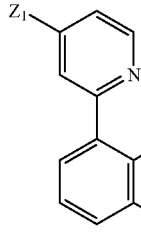
Formula 3-1(40)

Formula 3-1(41)
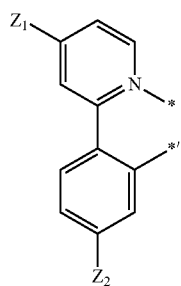
Formula 3-1(42)
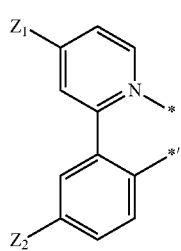
Formula 3-1(43)
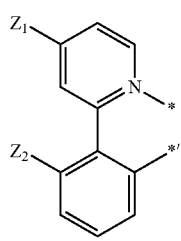
Formula 3-1(44)
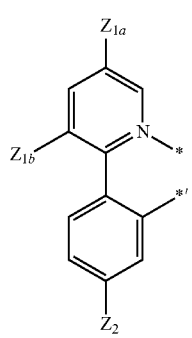
Formula 3-1(45)
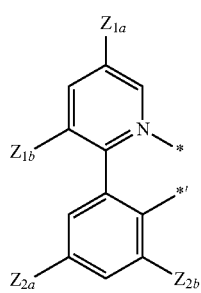
Formula 3-1(46)
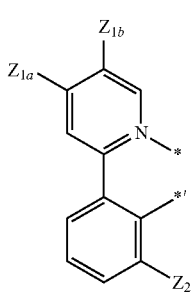
Formula 3-1(47)
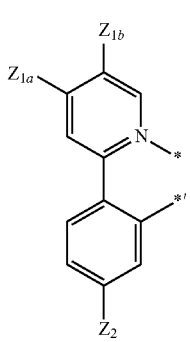
Formula 3-1(48)
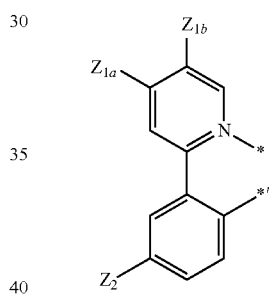
Formula 3-1(49)
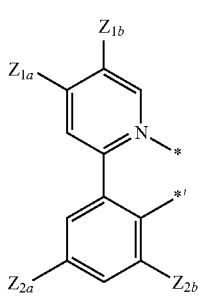
Formula 3-1(50)
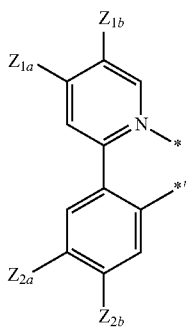

-continued
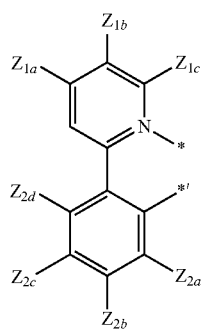
Formula 3-1(51)
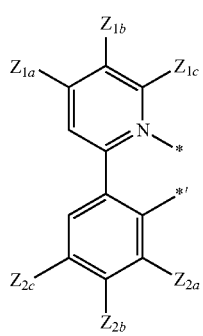
Formula 3-1(52)
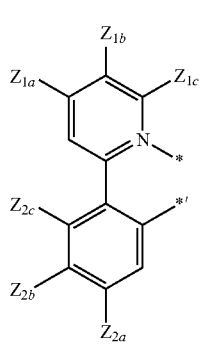
Formula 3-1(53)
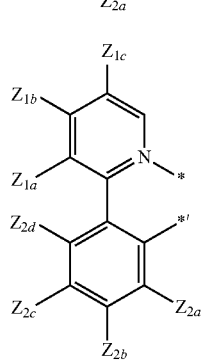
Formula 3-1(54)
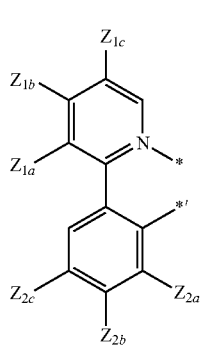
Formula 3-1(55)
-continued
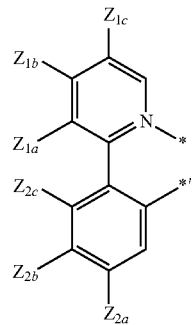
Formula 3-1(56)
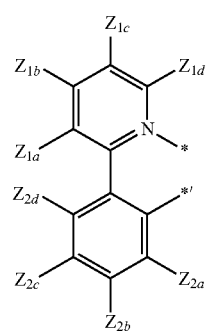
Formula 3-1(57)
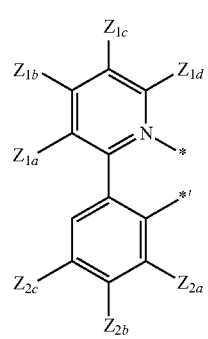
Formula 3-1(58)
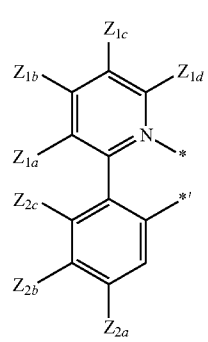
Formula 3-1(59)

-continued
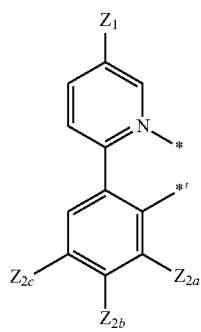
Formula 3-1(60)
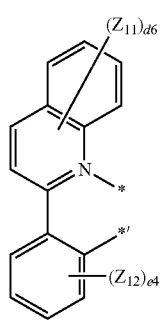
Formula 3-1(61)
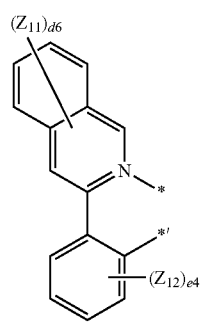
Formula 3-1(62)
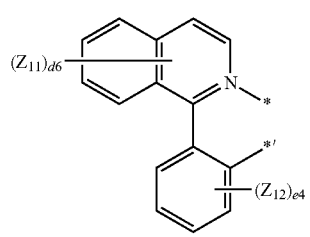
Formula 3-1(63)
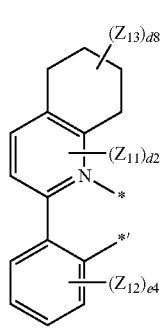
Formula 3-1(64)
-continued
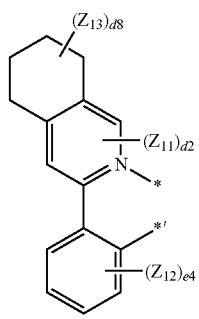
Formula 3-1(65)
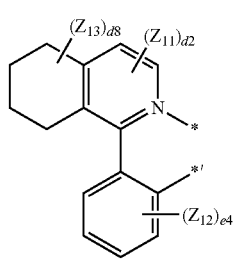
Formula 3-1(66)
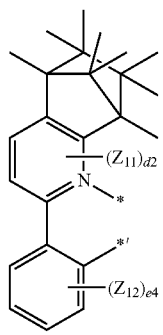
Formula 3-1(67)
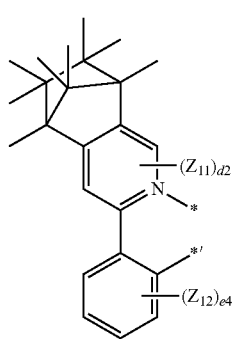
Formula 3-1(68)
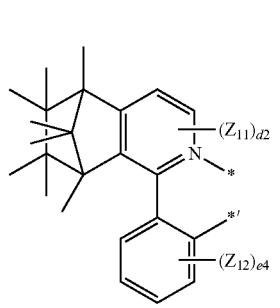
Formula 3-1(69)

-continued
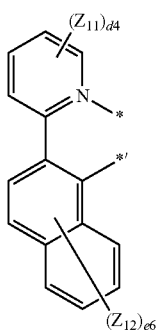
Formula 3-1(71)
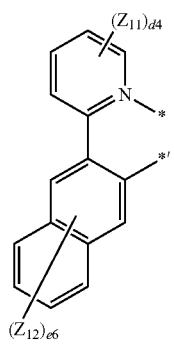
Formula 3-1(72)
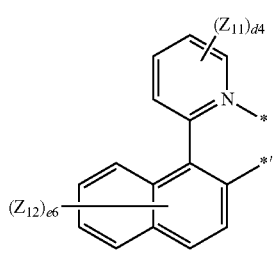
Formula 3-1(73)
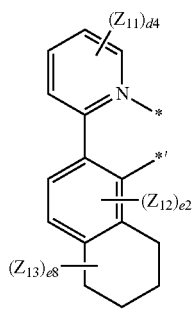
Formula 3-1(74)
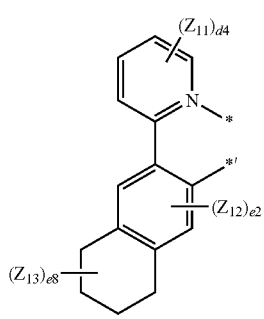
Formula 3-1(75)
-continued
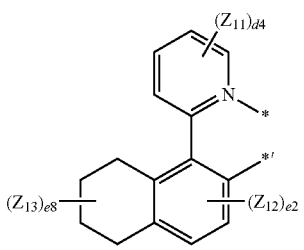
Formula 3-1(76)
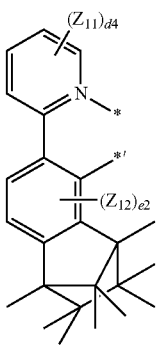
Formula 3-1(77)
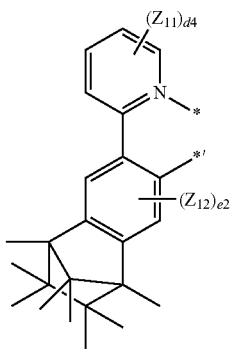
Formula 3-1(78)
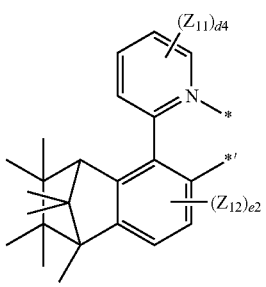
Formula 3-1(79)
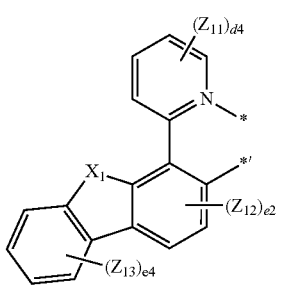
Formula 3-1(81)

Formula 3-1(82)
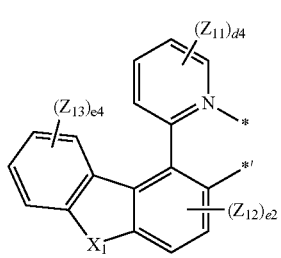
Formula 3-1(83)
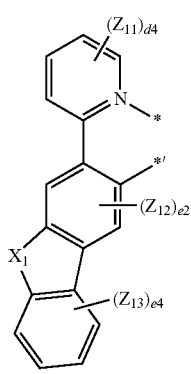
Formula 3-1(84)
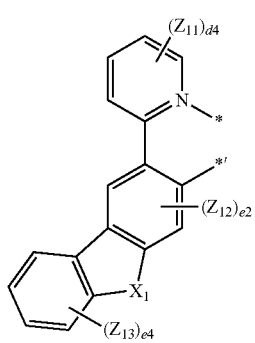
Formula 3-1(85)
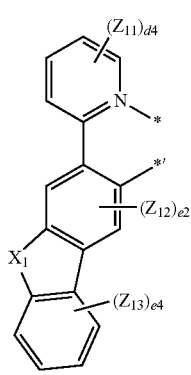
Formula 3-1(86)
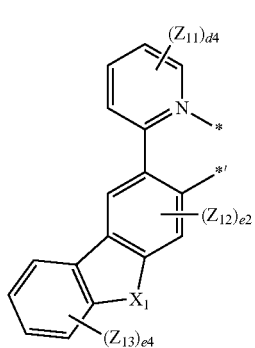
Formula 3-1(87)
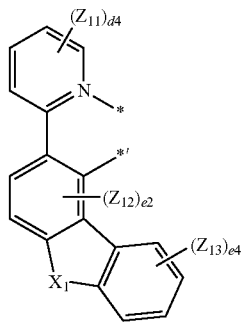
Formula 3-1(88)
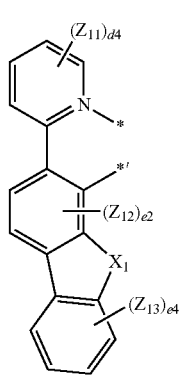
Formula 3-1(91)
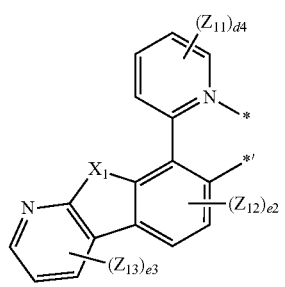
Formula 3-1(92)
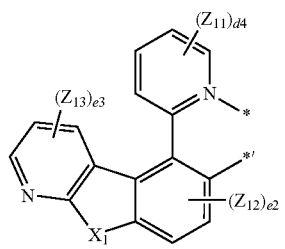
Formula 3-1(93)

Formula 3-1(94)
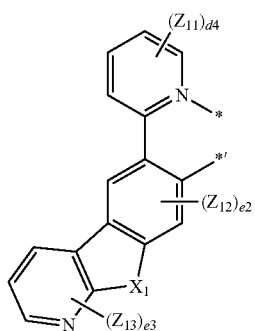
Formula 3-1(95)
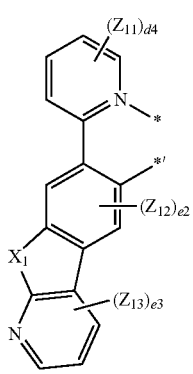
Formula 3-1(96)
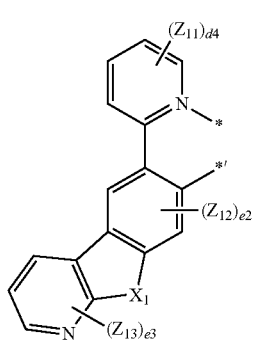
Formula 3-1(97)
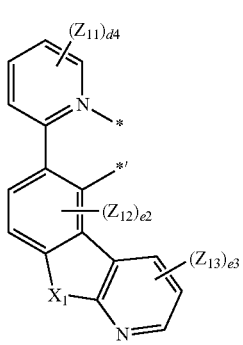
Formula 3-1(98)
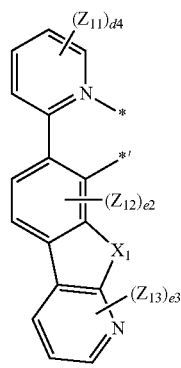
Formula 3-1(101)
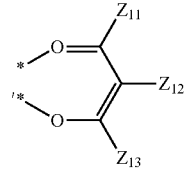
Formula 3-1(102)
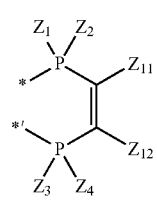
Formula 3-1(103)
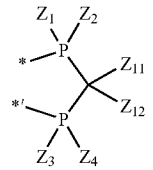
Formula 3-1(104)
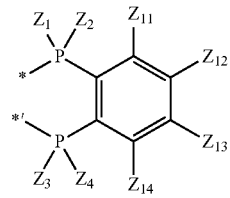
Formula 3-1(105)
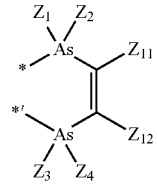
Formula 3-1(106)
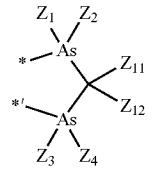

-continued

Formula 3-1(107)

Formula 3-1(108)

Formula 3-1(109)

Formula 3-1(110)

Formula 3-1(111)

Formula 3-1(112)

Formula 3-1(113)

Formula 3-1(114)

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, $X_{32}$ may be N or $C(Z_{1b})$, $X_{41}$ may be O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_{86}$)(Q$_{87}$) and —P(=O)(Q$_{88}$)(Q$_{89}$), Q$_{86}$ to Q$_{89}$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD2CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, d2 and e2 may each independently be 0 or 2, e3 may be an integer selected from 0 to 3, d4 and e4 may each independently be an integer selected from 0 to 4, d6 and e6 may each independently be an integer selected from 0 to 6, d8 and e8 may each independently be an integer selected from 0 to 8, and

* and *' each indicate a binding site to M of Formula 1.

For example, Z$_1$ to Z$_4$, Z$_{1a}$, Z$_{1b}$, Z$_{1c}$, Z$_{1d}$, Z$_{2a}$, Z$_{2b}$, Z$_{2c}$, Z$_{2d}$, Z$_{11}$ to Z$_{14}$, and Z$_{21}$ to Z$_{23}$ may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, but embodiments are not limited thereto.

In various embodiments, in Formula 81,

M may be Ir, and the sum of n81 and n82 may be 3; or

M may be Pt, and the sum of n81 and n82 may be 2.

In various embodiments, the organometallic compound represented by Formula 81 may be an electrically neutral compound, rather than a salt consisting of a pair of a cation and an anion.

The phosphorescent dopant may include at least one selected from Compounds PD1 to PD79 and FIr6, but embodiments are not limited thereto:

PD1
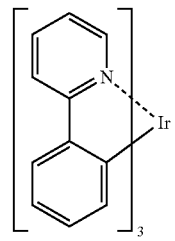

PD2
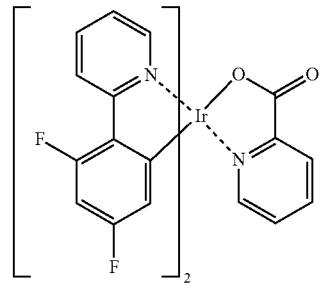

PD3
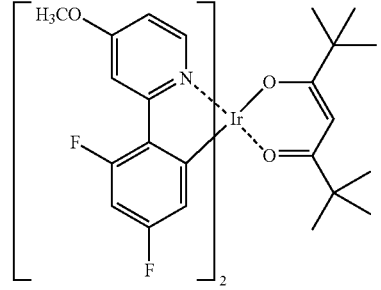

PD4
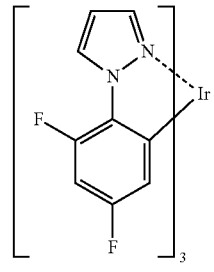

PD5
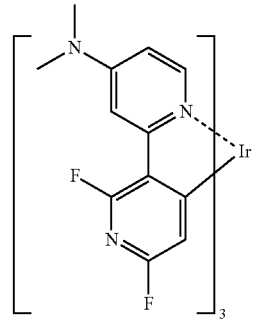

-continued
PD6
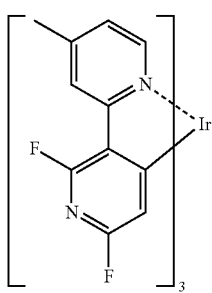
PD7
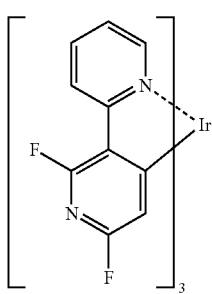
PD8
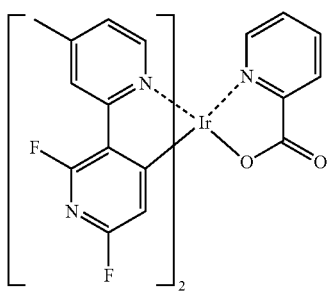
PD9
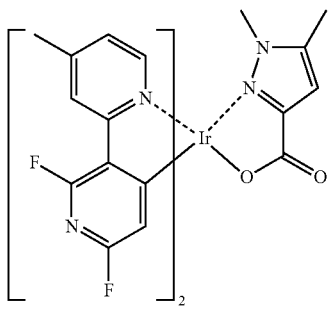
PD10
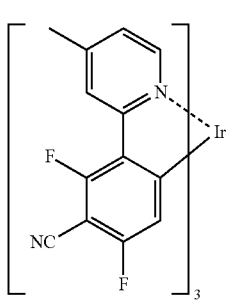
-continued
PD11
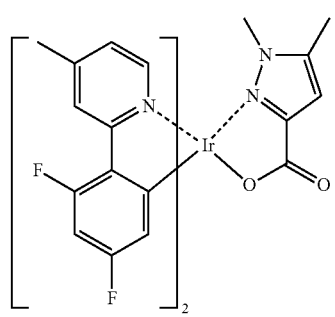
PD12
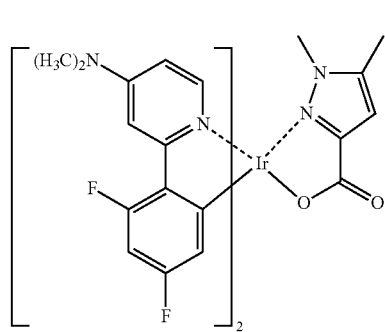
PD13
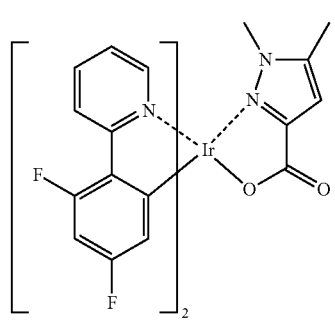
PD14
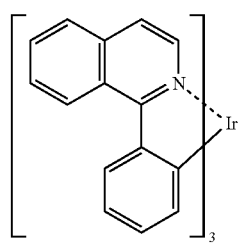
PD15
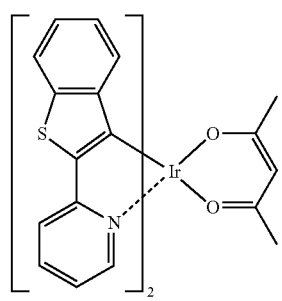

PD16
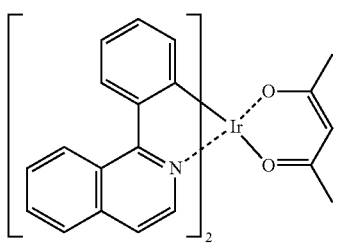
PD17
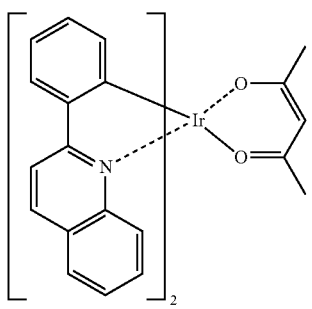
PD18
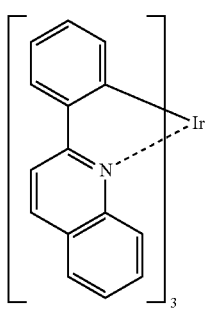
PD19
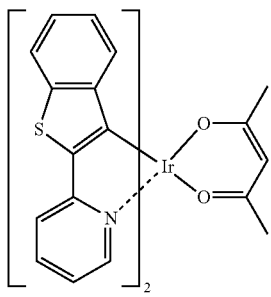
PD20
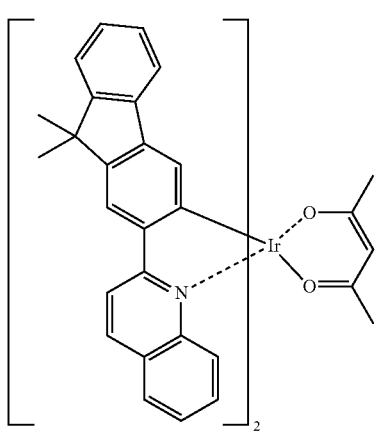
PD21
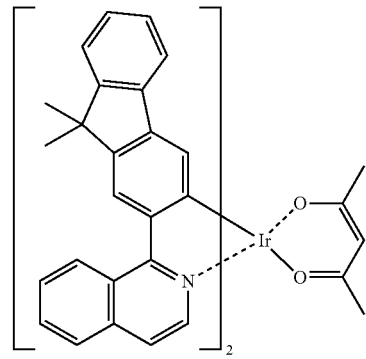
PD22
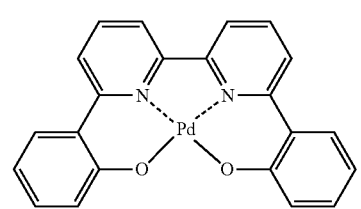
PD23
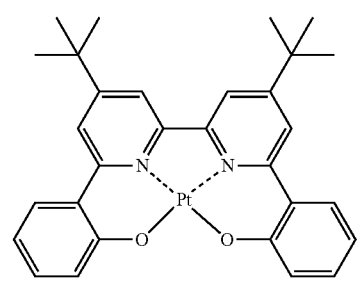
PD24
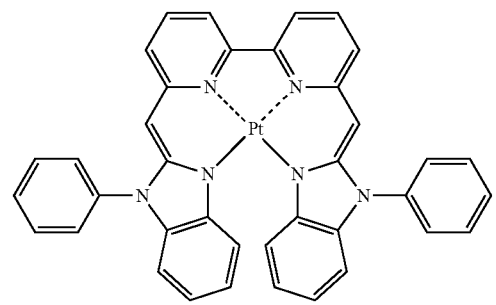
PD25
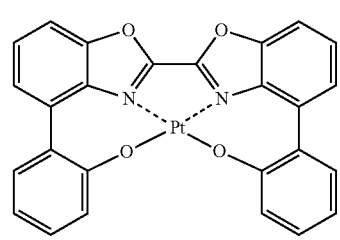
PD26
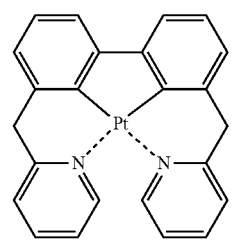

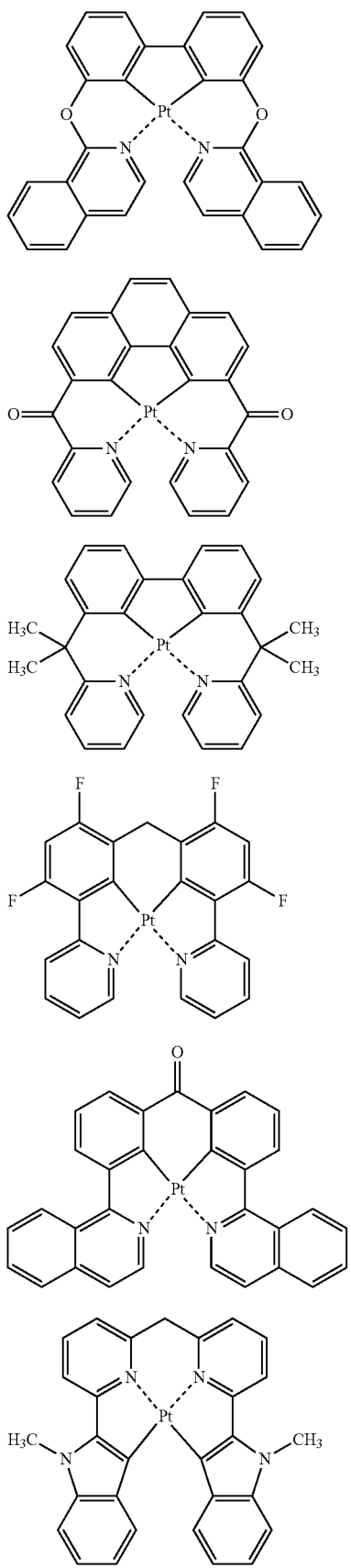
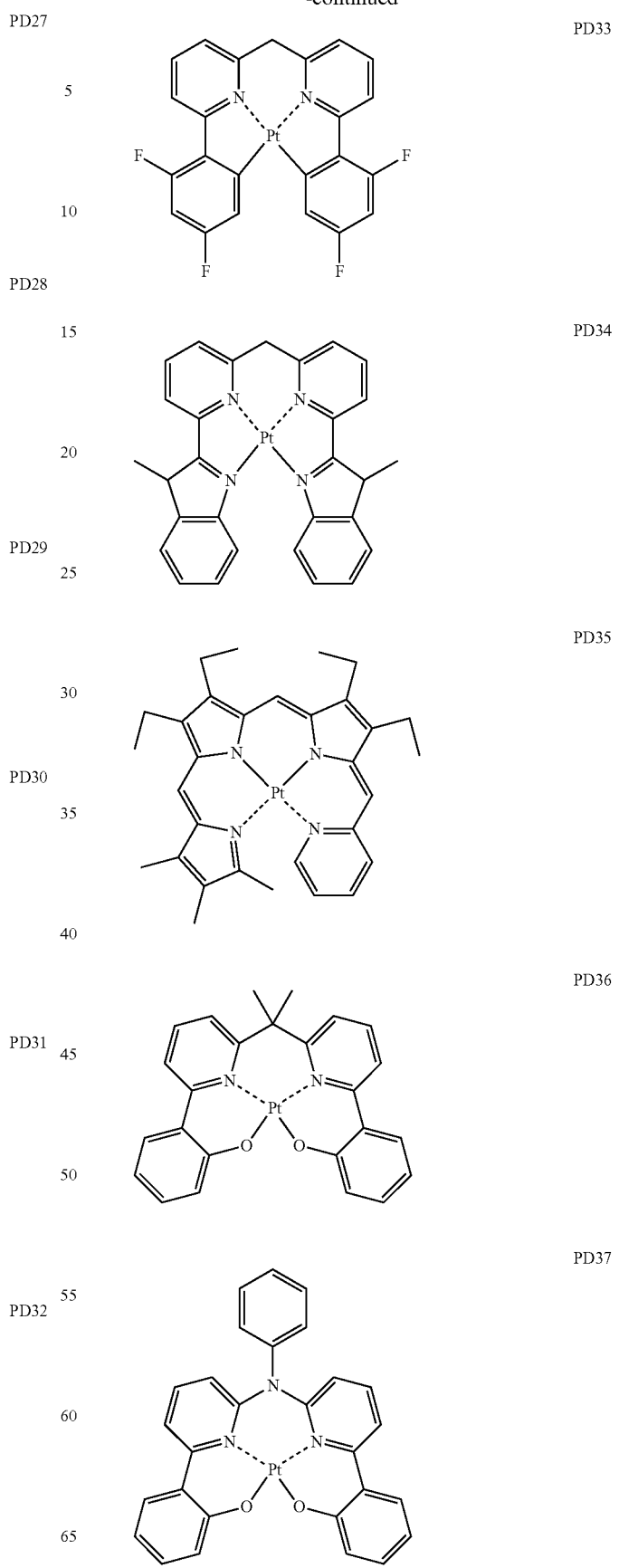

-continued
PD38
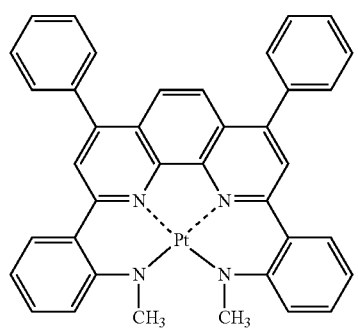
PD39
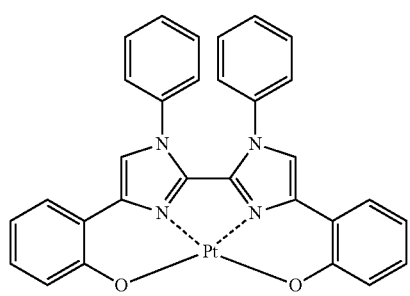
PD40
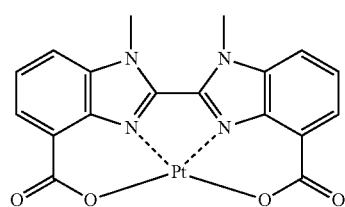
PD41
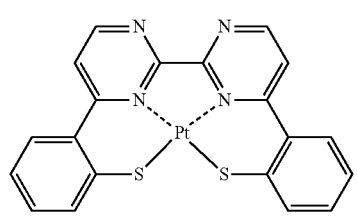
PD42
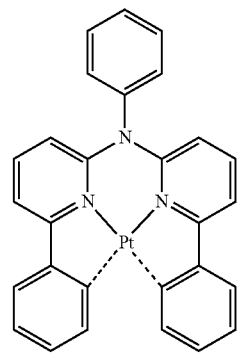
-continued
PD43
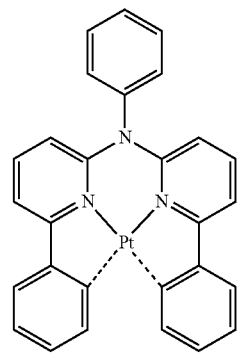
PD44
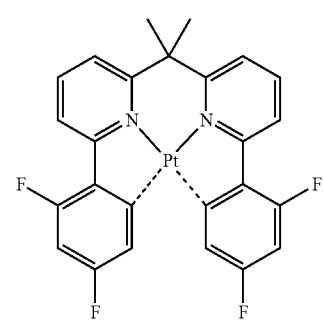
PD45
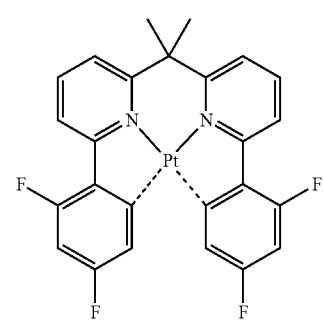
PD46
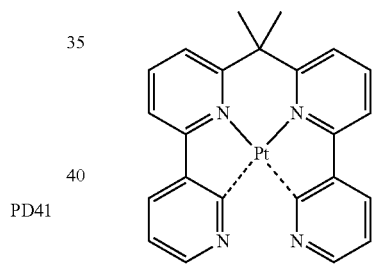
PD47
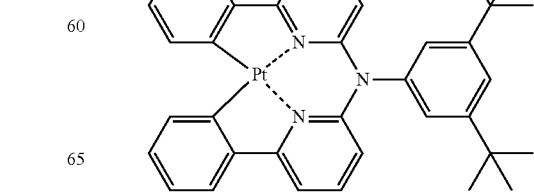

PD48 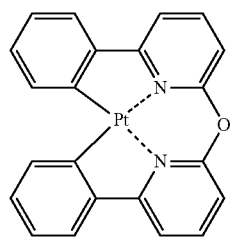
PD49 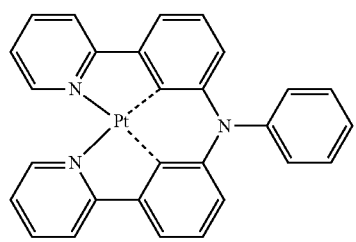
PD50 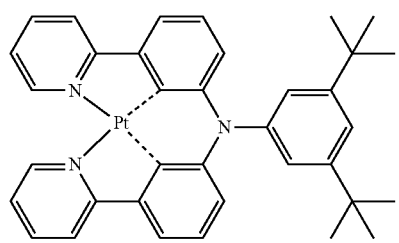
PD51 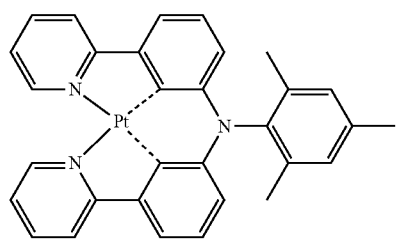
PD52 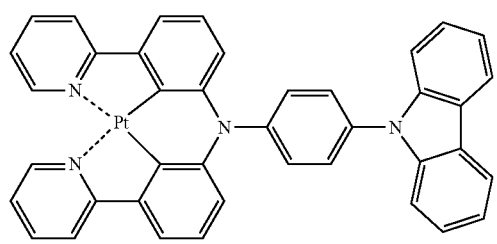
PD53 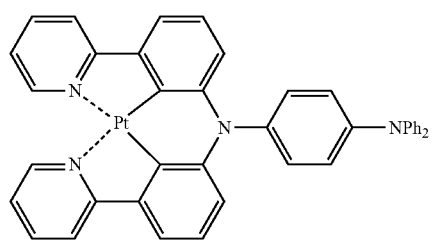
PD54 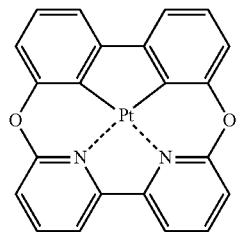
PD55 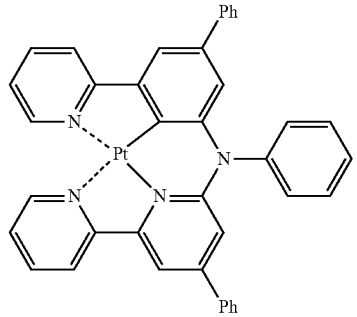
PD56 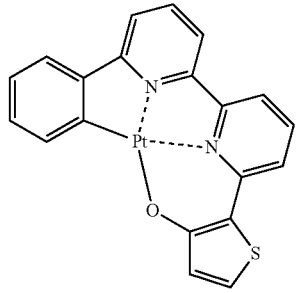
PD57 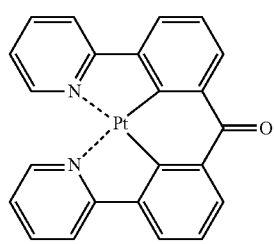
PD58 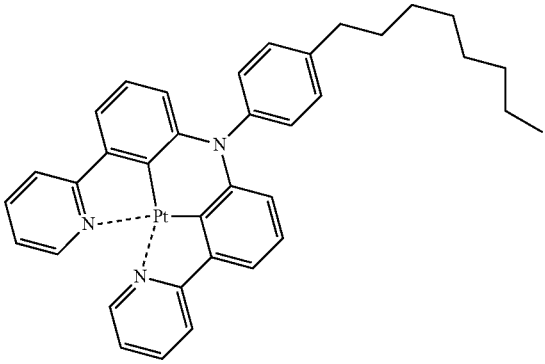

-continued
PD59
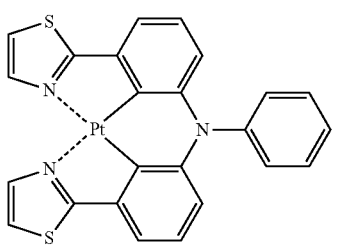
PD60
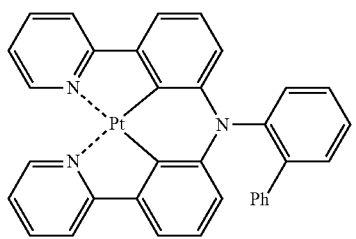
PD61
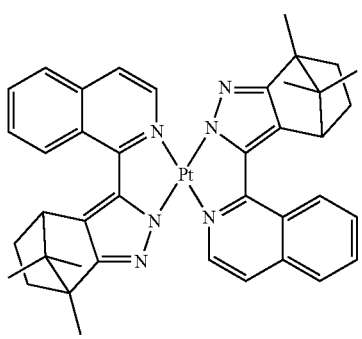
PD62
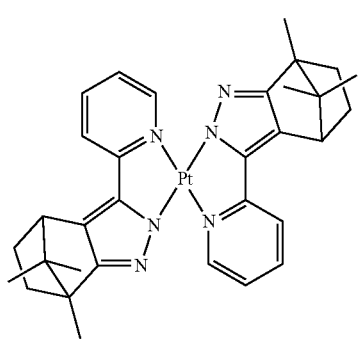
PD63
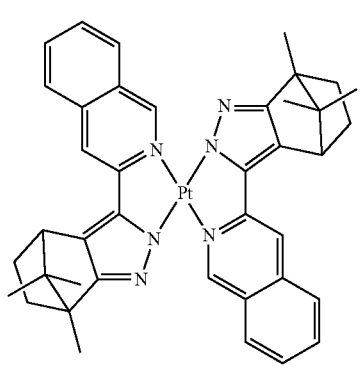
-continued
PD64
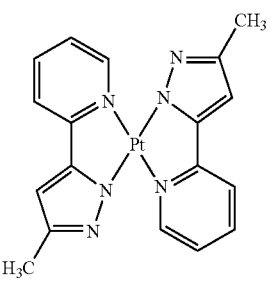
PD65
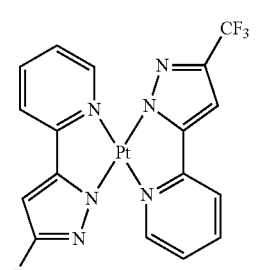
PD66
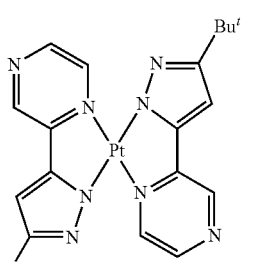
PD67
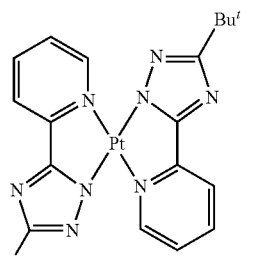
PD68
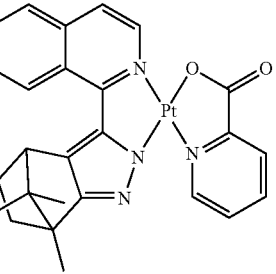

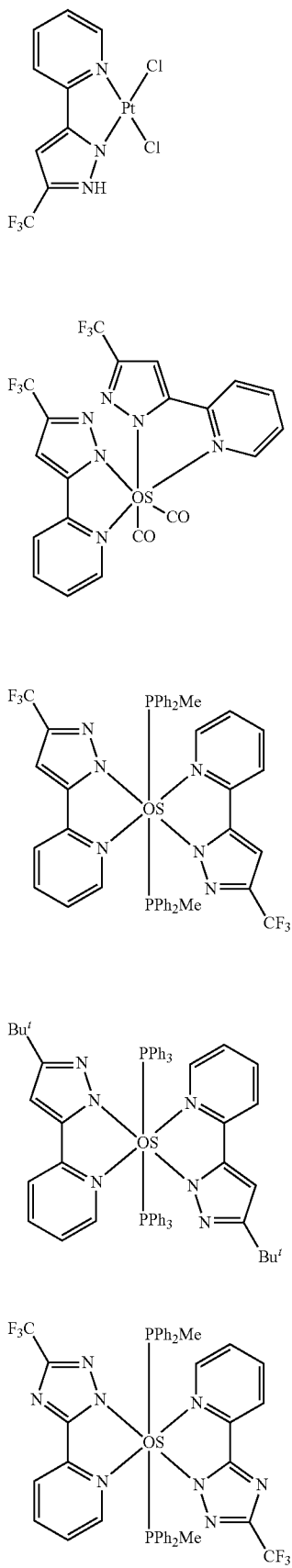

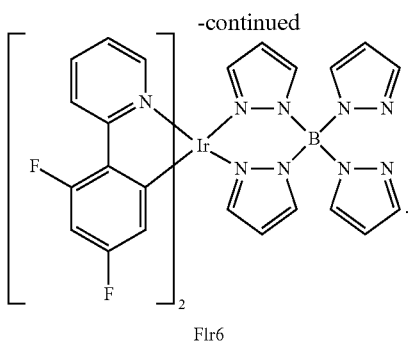

Flr6

In various embodiments, the phosphorescent dopant may include PtOEP:

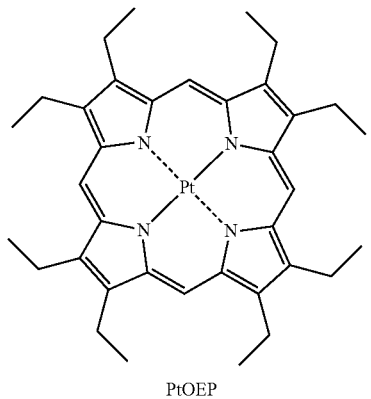

PtOEP

When the emission layer includes a host and a dopant, an amount of the dopant may be generally in a range of about 0.01 to about 20 parts by weight based on 100 parts by weight, but embodiments are not limited thereto.

A thickness of the emission layer may be in a range of about 100 Å to about 1,000 Å, for example, about 200 Å to about 600 Å. While not wishing to be bound by theory, it is understood that when the thickness of the emission layer is within these ranges, excellent light-emitting characteristics may be obtained without a substantial increase in driving voltage.

Next, the electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more materials.

Conditions for forming a hole blocking layer, an electron transport layer, and an electron injection layer of the electron transport region may be understood by referring to conditions for forming the hole injection layer.

When the electron transport region includes a hole blocking layer, the hole blocking layer may include, for example, at least one of BCP and Bphen, but embodiments are not limited thereto:

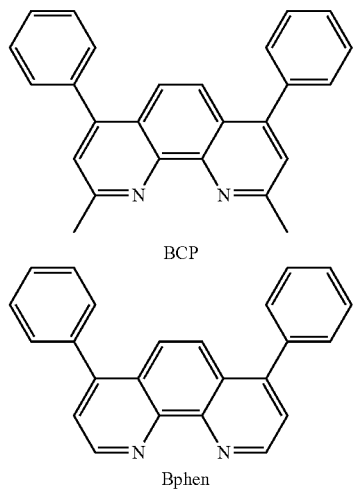

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, excellent hole blocking characteristics may be obtained without a substantial increase in driving voltage.

The electron transport layer may further include at least one selected from BCP, Bphen, Alq$_3$, BAlq, TAZ, and NTAZ:

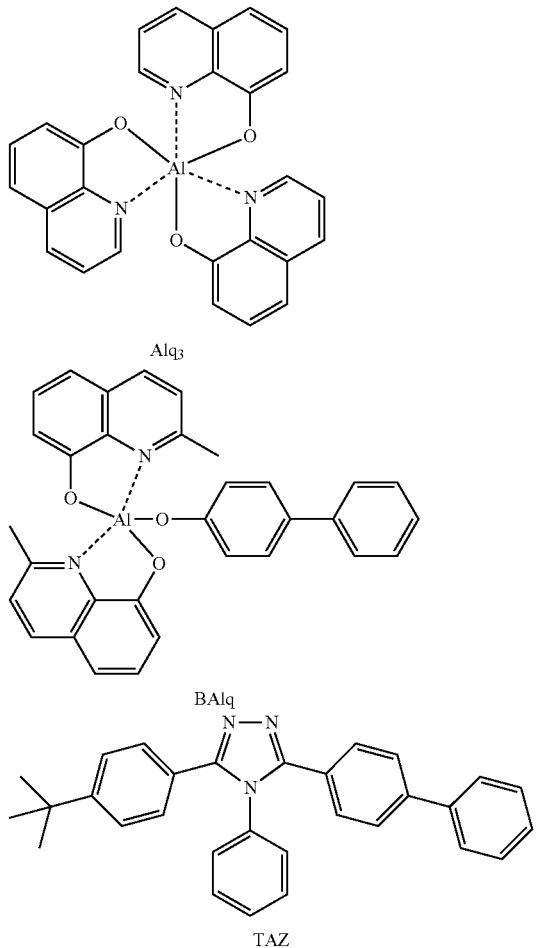

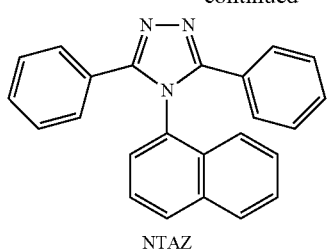

NTAZ

In some embodiments, the electron transport layer may include at least one selected from Compounds ET1, ET2, and ET3, but embodiments are not limited thereto:

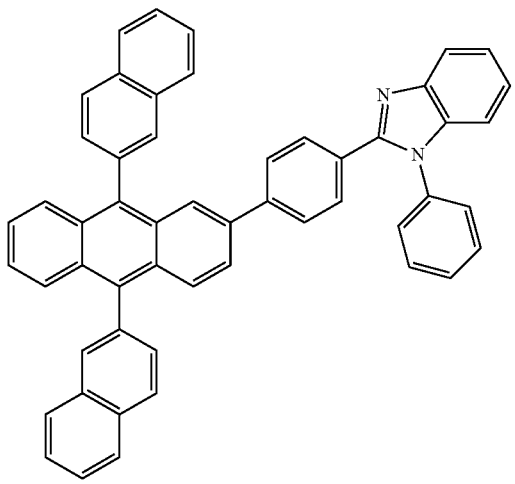

ET1

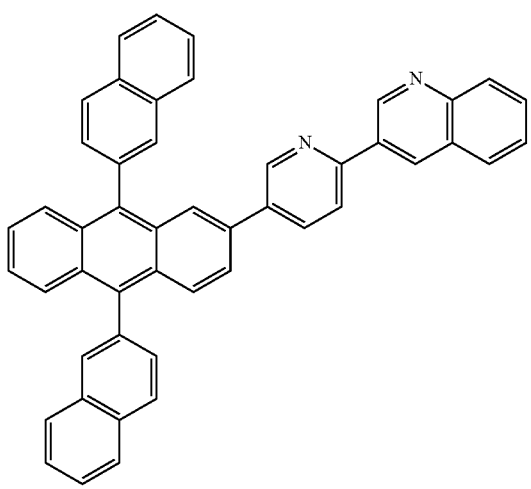

ET2

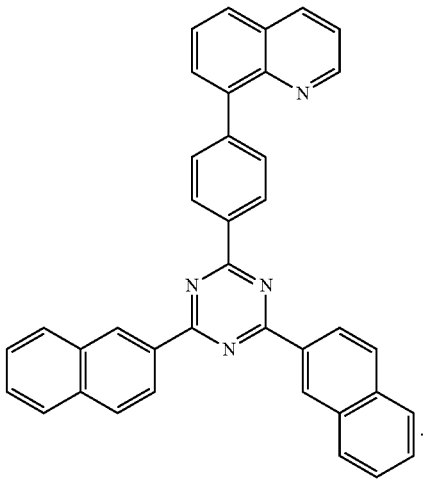

ET3

A thickness of the electron transport layer may be in a range of about 100 Å to about 1,000 Å, for example, about 150 Å to about 500 Å. While not wishing to be bound by theory, it is understood that when the thickness of the electron transport layer is within these ranges, satisfactory electron transporting characteristics may be obtained without a substantial increase in driving voltage.

The electron transport layer may further include, in addition to these materials, a metal-containing material.

The metal-containing material may include a lithium (Li) complex. The Li complex may include, for example, Compound ET-D1 (lithium quinolate LiQ)) or Compound ET-D2:

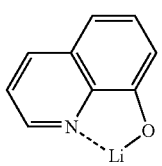

ET-D1

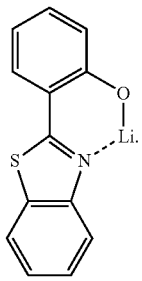

ET-D2

In addition, the electron transport region may include an electron injection layer that facilitates electron injection from the second electrode 19.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within these ranges, satisfactory electron injecting characteristics may be obtained without a substantial increase in driving voltage.

The second electrode 19 may be disposed on the organic layer 15. The second electrode 19 may be a cathode. A material for forming the second electrode 19 may be a metal having a relatively low work function, an alloy, an electrically conductive compound, and a combination thereof. For example, Li, Mg, Al, Al—Li, Ca, Mg—In, or Mg—Ag may be used as a material for forming the second electrode 19. In various embodiments, to manufacture a top emission-type light-emitting device, a transmissive electrode formed using ITO or IZO may be used as the second electrode 19.

Hereinbefore, the organic light-emitting device 10 has been described with reference to FIG. 1, but is not limited thereto.

A $C_1$-$C_{60}$ alkyl group as used herein refers to a linear or branched aliphatic saturated hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Examples thereof include a methoxy group, an ethoxy group, and an iso-propyloxy (iso-propoxy) group.

A $C_2$-$C_{60}$ alkenyl group as used herein refers to a hydrocarbon group formed by including at least one carbon-carbon double bond in the middle or at either terminal end of the $C_2$-$C_{60}$ alkyl group. Examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by including at least one carbon-carbon triple bond in the middle or at either terminal end of the $C_2$-$C_{60}$ alkyl group. Examples thereof include an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent saturated hydrocarbon monocyclic group having 3 to 10 carbon atoms. Examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent saturated monocyclic group having at least one heteroatom selected from N, O, P, Si, and S as a ring-forming atom and 1 to 10 carbon atoms. Examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one carbon-carbon double bond in the ring thereof, and which is not aromatic. Examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, Si, and S as a ring-forming atom, 1 to 10 carbon atoms, and at least one carbon-carbon double bond in the ring. Examples of the $C_1$-$C_{10}$ heterocycloalkenyl group include a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the respective rings may be fused to each other.

A $C_1$-$C_{60}$ heteroaryl group as used herein refers to a monovalent group having a heterocyclic aromatic system that has at least one heteroatom selected from N, O, P, Si, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, Si, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the respective rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group (for example, a group having 8 to 60 carbon atoms) that has two or more rings condensed to each other, only carbon atoms as a ring forming atom, and which is non-aromatic in the entire molecular structure. An example of the non-aromatic condensed polycyclic group includes a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, a group having 2 to 60 carbon atoms) that has two or more rings condensed to each other, has a heteroatom selected from N, O, P, Si, and S, other than carbon atoms, as a ring-forming atom, and which is non-aromatic in the entire molecular structure. An example of the monovalent non-aromatic condensed heteropolycyclic group includes a carbazolyl group. A divalent non-aromatic condensed heteropolycyclic group as used herein refers to a divalent group having the same structure as the monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "biphenyl group" as used herein refers to a monovalent group in which two benzene groups are linked via a single bond.

The term "terphenyl group" as used herein refers to a monovalent group in which three benzene groups are linked via a single bond.

Hereinafter, a compound according to embodiments and an organic light-emitting device according to embodiments will be described in detail with reference to Synthesis Examples and Examples below, but the present inventive concept is not limited thereto. The expression "'B' was used instead of 'A'" used in describing Synthesis Examples below means that the number of molar equivalents of 'B' used was identical to the number of molar equivalents of 'A'.

EXAMPLES

Synthesis Example 1

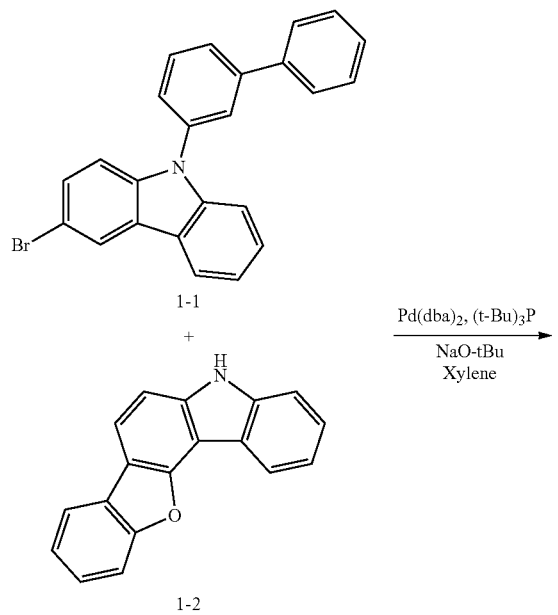

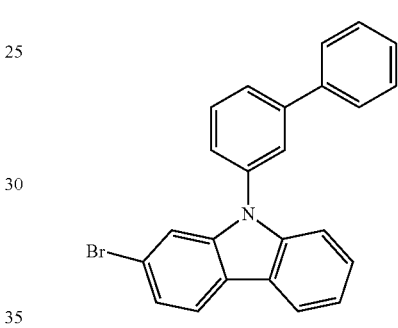

10 grams (g) (25.1 millimoles, mmol) of Intermediate 1-1 (i.e., 9-(meta-biphenyl)-3-bromo-9H-carbazole), 6.78 g of Intermediate 1-2 (i.e., 5H-benzofuro[3,2-c]carbazole), 0.92 g of Pd(dba)$_2$, 1.4 milliliters (ml) of P(tBu)$_3$ in toluene, and 2.9 g of NaO-tBu were added to a 500 ml 2-neck round-bottomed flask, followed by 150 ml of toluene. The mixed solution was stirred at a temperature of 105° C. for 18 hours. The mixed reaction solution was cooled, a worked-up using water and a dichloromethane, dried over MgSO$_4$, and concentrated. The resulting reaction product was purified by silica gel column chromatography to give 12 g of pale yellow solid, which was recrystallized using methyl chloride (MC)/ethyl acetate (EA), to thereby obtain 9.2 g (yield: 71%) of Compound 1. The synthesized compound was identified using LC-MS.

LC-Mass (calc.: 574.20, found: [M+H]$^+$ 575.21).

Synthesis Example 2

Compound 2 (yield: 68%) was synthesized in the same manner as in Synthesis Example 1, except that Intermediate 2-1 was used instead of Intermediate 1-1. The synthesized compound was identified using LC-MS.

LC-Mass (calc.: 574.20, found: [M+H]$^+$ 575.20).

Synthesis Example 3

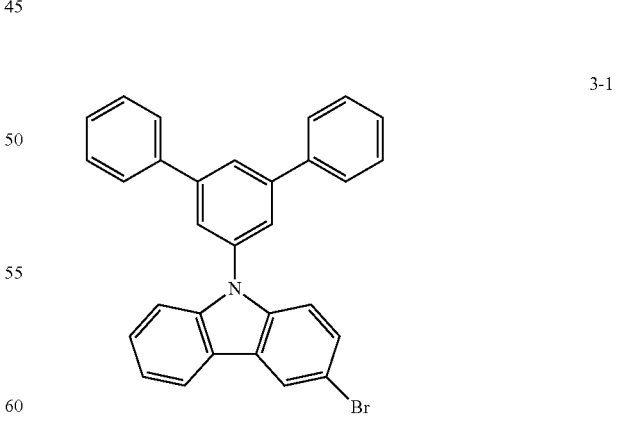

Compound 3 (yield: 58%) was synthesized in the same manner as in Synthesis Example 1, except that Intermediate 3-1 was used instead of Intermediate 1-1. The synthesized compound was identified using LC-MS.

LC-Mass (calc.: 650.24, found: [M+H]$^+$ 651.24).

Synthesis Example 4

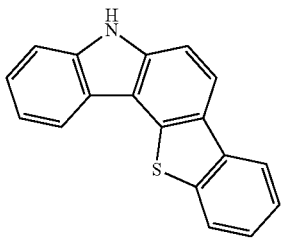

4-2

Compound 4 (yield: 63%) was synthesized in the same manner as in Synthesis Example 1, except that Intermediate 4-2 was used instead of Intermediate 1-2. The synthesized compound was identified using LC-MS.

LC-Mass (calc.: 590.18, found: [M+H]$^+$ 591.19).

Synthesis Example 5

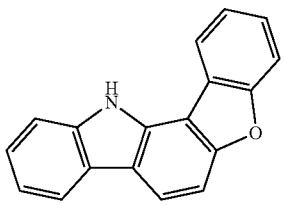

9-2

Compound 9 (yield: 51%) was synthesized in the same manner as in Synthesis Example 2, except that Intermediate 9-2 was used instead of Intermediate 1-2. The synthesized compound was identified using LC-MS.

LC-Mass (calc.: 574.20, found: [M+H]$^+$ 575.20).

Synthesis Example 6

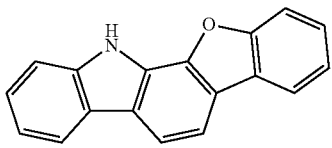

11-2

Compound 11 (yield: 65%) was synthesized in the same manner as in Synthesis Example 1, except that Intermediate 11-2 was used instead of Intermediate 1-2. The synthesized compound was identified using LC-MS.

LC-Mass (calc.: 574.20, found: [M+H]$^+$ 575.20).

Evaluation Example 1: Evaluation of HOMO and LUMO Energy Levels

According to methods described in Table 2, the HOMO and the LUMO energy levels and the T$_1$ energy levels of Compounds 1, 2, 3, 4, 9, and 11 and Compounds D, E, and F were evaluated, and the results are shown in Table 3.

TABLE 2

| | |
|---|---|
| HOMO energy level evaluation | Cyclic voltammetry (CV) (electrolyte: 0.1 molar (M) Bu$_4$NPF$_6$/ solvent: CH$_2$Cl$_2$/electrode: 3-electrode system (operation electrode: Pt disc (1 millimeters (mm) diameter), standard electrode: Pt wire, auxiliary electrode: Pt wire)) was used to obtain a potential (V)-current (A) graph for each compound, to there by calculate HOMO energy levels for each compound based on an oxidation onset on the graph. |
| LUMO energy level evaluation | Each compound was diluted with CHCl$_3$ at a concentration of 1 × 10$^{-5}$ molar (M), and a Shimadzu UV-350 spectrometer was used to measure a UV absorption spectrum for each compound at room temperature, to thereby calculate LUMO energy levels for each compound based on the optical band gap (Eg) at edges of the absorption spectrum and HOMO energy levels for each compound. |
| T$_1$ energy level evaluation | A mixture of 2-MeTHF and each compound (i.e., a mixture prepared by dissolving 1 mg of each compound in 3 cubic centimeters (cc) of 2-MeTHF) was loaded into a quartz cell. The resulting quartz cell was loaded into liquid nitrogen (77 Kelvins, K), and a photoluminescence spectrum thereof was measured by using a photoluminescence measuring meter. Then, T$_1$ energy levels were calculated based on peaks observed at the beginning of short wavelengths of the photoluminescence spectrum wavelengths. |

TABLE 3

| Compound No. | HOMO (eV) | LUMO (eV) | T$_1$ (eV) |
|---|---|---|---|
| 1 | −5.56 | −2.15 | 3.05 |
| 2 | −5.64 | −2.39 | 3.05 |
| 3 | −5.51 | −2.33 | 2.80 |
| 4 | −5.56 | −2.19 | 2.84 |
| 9 | −5.66 | −2.14 | 2.87 |
| 11 | −5.53 | −2.13 | 2.84 |
| D | −5.56 | −2.82 | 2.77 |
| E | −5.44 | −2.05 | 2.79 |
| F | −5.67 | −2.17 | 2.78 |

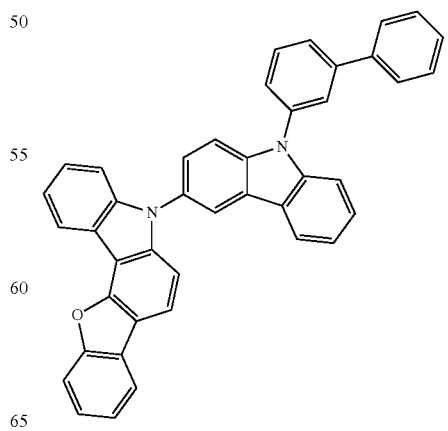

1

TABLE 3-continued
| Compound No. | HOMO (eV) | LUMO (eV) | $T_1$ (eV) |
|---|---|---|---|
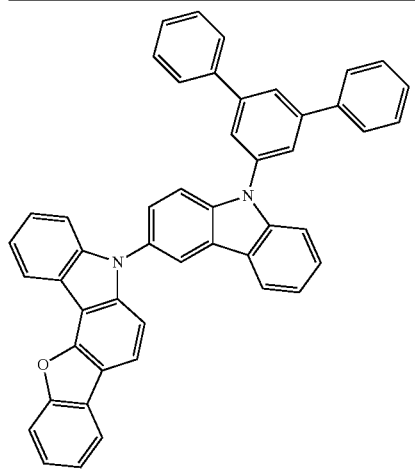
3
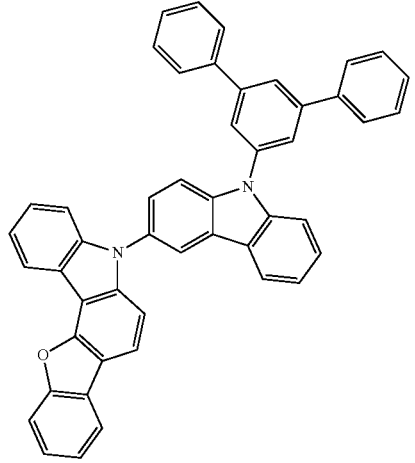
3
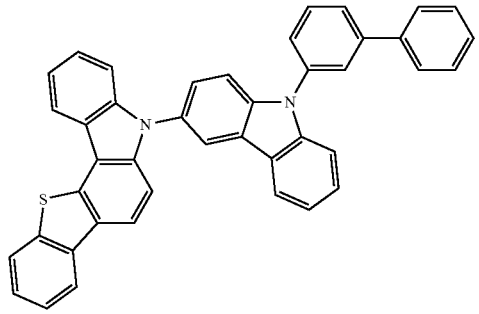
4
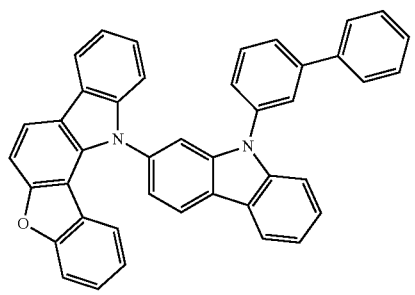
9
TABLE 3-continued
| Compound No. | HOMO (eV) | LUMO (eV) | $T_1$ (eV) |
|---|---|---|---|
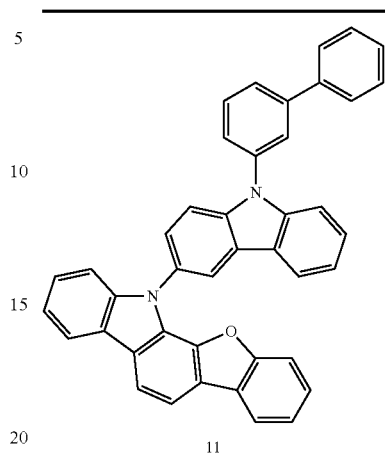
11
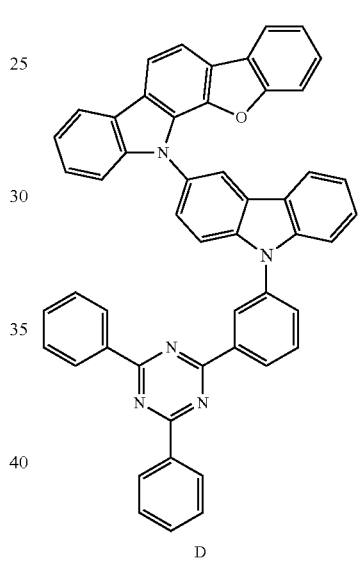
D
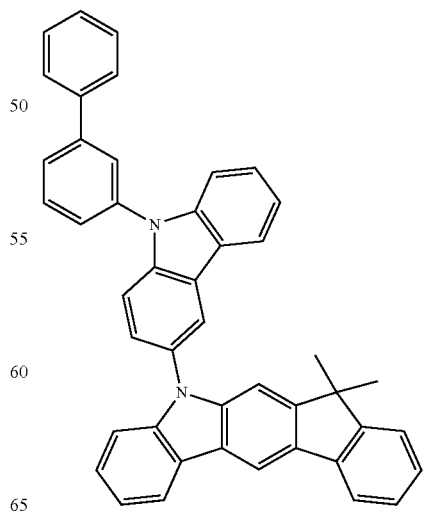
E TABLE 3-continued

| Compound No. | HOMO (eV) | LUMO (eV) | T₁ (eV) |
|---|---|---|---|

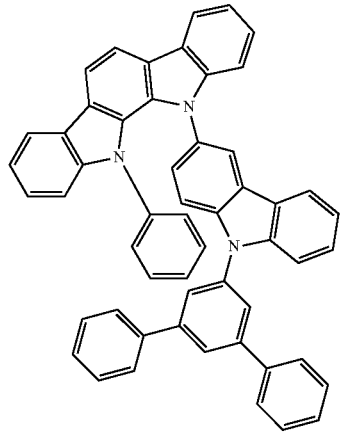

F

Referring to Table 3, it was determined that Compounds 1, 2, 3, 4, 9, and 11 had appropriate electric characteristics for use in the organic light-emitting device.

Evaluation Example 2: Evaluation of Thermal Characteristics

Compounds 1, 2, 4, 9, 11, and A' were subjected to thermo gravimetric analysis (TGA) and differential scanning calorimetry (DSC) to perform thermal analysis thereon (under conditions including $N_2$ atmosphere, temperature ranges from room temperature to 800° C. (10° C./min) for the TGA and from room temperature to 400° C. for the DSC, and Pan Type of Pt Pan in disposable Al Pan (for the TGA) and disposable Al pan (for the DSC)), and the results are shown in Table 4. Referring to Table 4, it was determined that Compounds 1, 2, 4, 9, and 11 had excellent thermal stability, compared to that of Compound A'.

TABLE 4

| Compound No. | Tg (° C.) |
|---|---|
| 1 | 132 |
| 2 | 129 |
| 4 | 140 |
| 9 | 124 |
| 11 | 128 |
| A' | 72 |

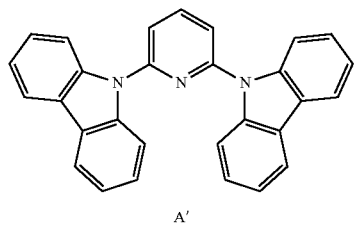 [SMILES: c1cc(-n2c3ccccc3c3ccccc32)nc(-n2c3ccccc3c3ccccc32)c1]

A'

Example 1

A glass substrate, on which an indium tin oxide (ITO) electrode having a thickness of 1,500 Angstroms (Å) was formed, was ultrasonically cleaned by using distilled water. After completing the washing of the glass substrate using distilled water, the glass substrate was ultrasonically washed again using iso-propyl alcohol, acetone, and methanol, and then, dried. The glass substrate was transported to a plasma washing machine, washed using oxygen plasma for 5 minutes, and then, transported to a vacuum evaporator.

Compounds HT3 and HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 150 Å, thereby forming a hole transport region.

Compound 1 (as a host) and Compound PD79 (as dopant having an amount of 10 percent by weight, wt %) were co-deposited on the hole transport region to form an emission layer having a thickness of 400 Å.

BCP was vacuum-deposited on the emission layer to form a hole blocking layer having a thickness of 100 Å, Compound ET3 and Liq were vacuum-deposited together on the hole blocking layer to form an electron transport layer having a thickness of 250 Å, and Liq was deposited on the electron transport layer to form an electron injection layer having a thickness of 5 Å. Then, Al was deposited on the electron injection layer to form an Al second electrode (i.e., a cathode) having a thickness of 1,000 Å, thereby completing the manufacture of an organic light-emitting device.

Examples 2 to 6 and Comparative Examples 1 to 7

Organic light-emitting devices of Examples 2 to 6 and Comparative Examples 1 to 7 were each manufactured in substantially the same manner as in Example 1, except that compounds for forming the electron blocking layer and the emission layer are changed as shown in Table 5.

Evaluation Example 3: Evaluation of Characteristics of Organic Light-Emitting Device The driving voltage, current density, luminous efficiency, power efficiency, quantum emission efficiency, and lifespan of the organic light-emitting devices of Examples 1 to 6 and Comparative Examples 1 to 7 were measured using a Keithley 2400 current-voltage meter and a Minolta Cs-1000A luminance meter, and the results are shown in Table 5. In Table 5, $T_{95}$ (at 500 candelas per square meter, $cd/m^2$) in the lifespan results means the time until the brightness of the organic light-emitting devices reaches about 95% of the initial brightness (100%).

TABLE 5

|  | Electron blocking layer | Host in emission layer | Driving voltage (V) | Luminous efficiency (cd/A) | Power Efficiency (lm/W) | Quantum emission efficiency (%) | Lifespan at $T_{95}$ (hr) |
|---|---|---|---|---|---|---|---|
| Example 1 | mCP | Compound 1 | 5.3 | 28.3 | 16.6 | 18.0 | 33 |
| Example 2 | mCP | Compound 3 | 5.5 | 27.9 | 15.9 | 17.7 | 27 |
| Example 3 | mCP | Compound 4 | 5.6 | 29.3 | 16.6 | 18.6 | 28 |
| Example 4 | mCP | Compound 11 | 5.8 | 28.3 | 15.4 | 18.0 | 31 |
| Example 5 | Compound 1 | Compound 1 | 4.3 | 12.1 | 8.8 | 7.7 | 65 |
| Example 6 | Compound 3 | Compound 3 | 4.8 | 18.4 | 12.0 | 11.7 | 30 |
| Comparative Example 1 | mCP | Compound A | 5.1 | 27.5 | 16.9 | 17.5 | 20 |
| Comparative Example 2 | mCP | Compound B | 5.9 | 18.2 | 9.7 | 11.6 | 11 |
| Comparative Example 3 | mCP | Compound C | 5.3 | 23.4 | 13.8 | 14.9 | 16 |
| Comparative Example 4 | mCP | Compound D | 6.6 | 10.8 | 5.2 | 6.9 | 25 |
| Comparative Example 5 | mCP | Compound E | 4.5 | 27.3 | 18.9 | 14.5 | 18 |
| Comparative Example 6 | mCP | Compound F | 6.0 | 25.5 | 13.3 | 13.5 | 22 |
| Comparative Example 7 | mCP | mCP | 6.6 | 25.6 | 12.1 | 13.6 | 8 |

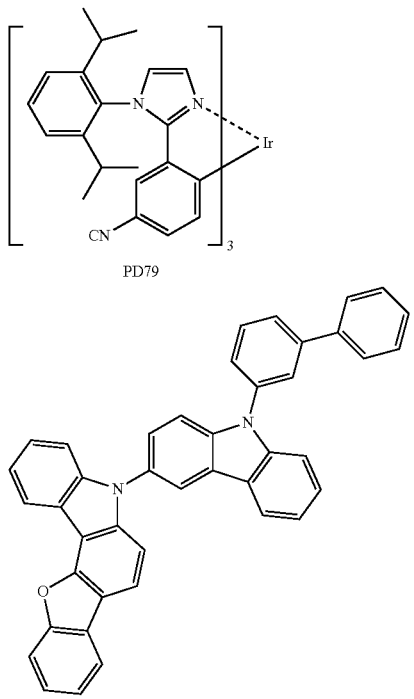

PD79

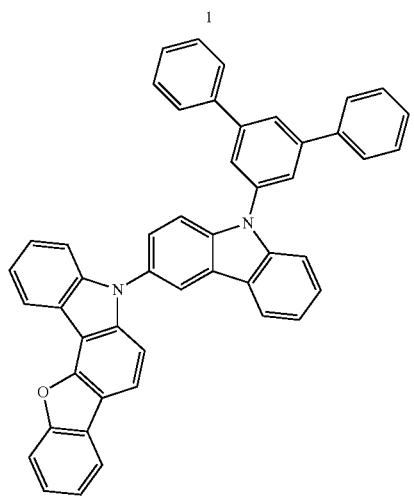

1

3

TABLE 5-continued

| Electron blocking layer | Host in emission layer | Driving voltage (V) | Luminous efficiency (cd/A) | Power Efficiency (lm/W) | Quantum emission efficiency (%) | Lifespan at $T_{95}$ (hr) |
| --- | --- | --- | --- | --- | --- | --- |

4

11

A

B

TABLE 5-continued
| Electron blocking layer | Host in emission layer | Driving voltage (V) | Luminous efficiency (cd/A) | Power Efficiency (lm/W) | Quantum emission efficiency (%) | Lifespan at $T_{95}$ (hr) |
|---|---|---|---|---|---|---|
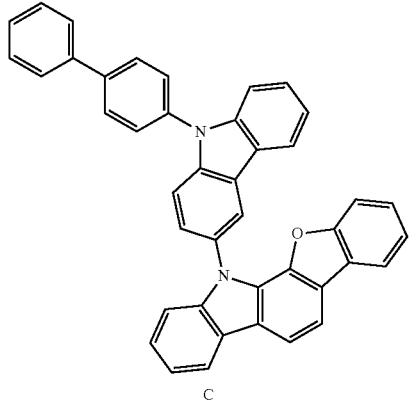
C
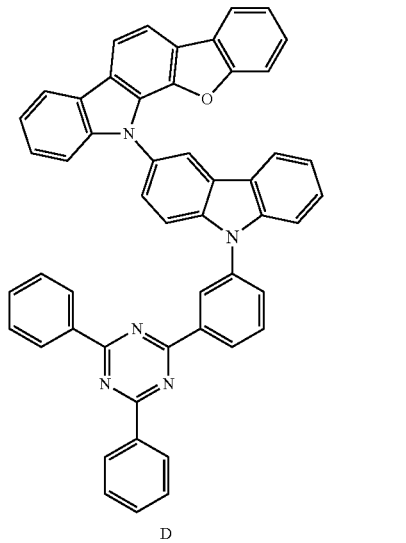
D
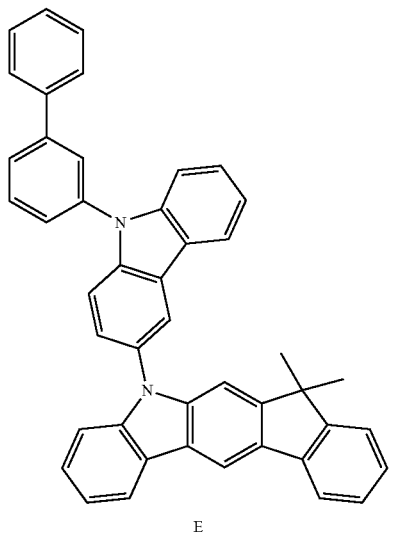 [SMILES: CC1(C)c2ccccc2-c2cc3c4ccccc4n(-c4ccc5c(c4)c4ccccc4n5-c4cccc(-c5ccccc5)c4)c3cc21]
E TABLE 5-continued

| | Electron blocking layer | Host in emission layer | Driving voltage (V) | Luminous efficiency (cd/A) | Power Efficiency (lm/W) | Quantum emission efficiency (%) | Lifespan at $T_{95}$ (hr) |
|---|---|---|---|---|---|---|---|

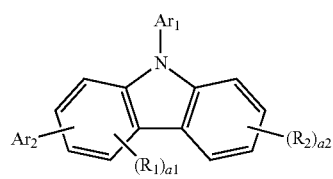

mCP

Referring to Table 5, it was determined that the organic light-emitting devices of Examples 1 to 6 had at least one selected from lower driving voltage, higher luminous efficiency, higher power efficiency, higher quantum emission efficiency, and longer lifespan, compared to the organic light-emitting devices of Comparative Examples 1 to 7.

As described above, a condensed cyclic compound represented by Formula 1 has excellent electric characteristics and thermal stability, and an organic light-emitting device including the condensed cyclic compound represented by Formula 1 has low driving voltage, high luminous efficiency, high power efficiency, high quantum emission efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:
1. An organic light-emitting device comprising:
a first electrode as an anode;
a second electrode as a cathode; and
an organic layer disposed between the first electrode and the second electrode,
wherein the organic layer comprises an emission layer,
wherein the organic layer further comprises a hole transport region disposed between the first electrode and the emission layer,
wherein the hole transport region comprises an electron blocking layer, and
wherein the electron blocking layer comprises a condensed cyclic compound represented by Formula 1:

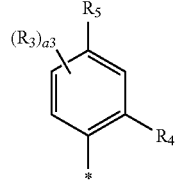

Formula 1

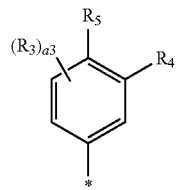

Formula 2A-1

Formula 2A-2

-continued

Formula 2A-3
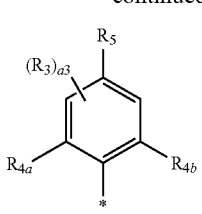

Formula 2A-4
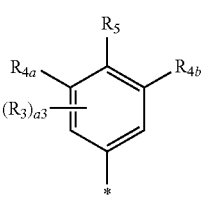

Formula 2A-5
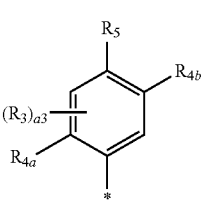

Formula 2B
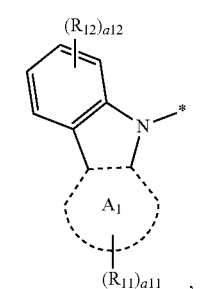

wherein, in Formula 1, $Ar_1$ is a group represented by Formulae 2A-1 to 2A-5, and $Ar_2$ is a group represented by Formula 2B, ring $A_1$ in Formula 2B is a dibenzofuran ring or a dibenzothiophene ring, $R_1$ to $R_3$, $R_{11}$, and $R_{12}$ in Formulae 1, 2A-1 to 2A-5, and 2B are each independently selected from:

hydrogen, deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one deuterium; and a phenyl group, a biphenyl group, a terphenyl group, a carbazolyl group, a pyridinyl group, a dibenzofuranyl group, a dibenzothiophenyl group, and a dibenzosilolyl group, each substituted with at least one selected from deuterium, a $C_1$-$C_{20}$ alkyl group, a $C_1$-$C_{20}$ alkoxy group, a phenyl group, a biphenyl group, a terphenyl group, a carbazolyl group, a pyridinyl group, a dibenzofuranyl group, a dibenzothiophenyl group, and a dibenzosilolyl group, a1 in Formula 1 is an integer selected from 0 to 3, wherein, when a1 is two or more, two or more groups $R_1$ are identical to or different from each other, a3 in Formulae 2A-1 to 2A-5 is an integer selected from 0 to 2, wherein when a3 is two or more, two or more groups $R_3$ are identical to or different from each other, a2 and a12 in Formulae 1 and 2B are each independently an integer selected from 0 to 4, wherein, when a2 is two or more, two or more groups $R_2$ are identical to or different from each other, and when a12 is two or more, two or more groups $R_{12}$ are identical to or different from each other, a11 in Formula 2B is an integer selected from 0 to 6, wherein, when a11 is two or more, two or more groups $R_{11}$ are identical to or different from each other, $R_4$, $R_{4a}$, and $R_{4b}$ are each independently selected from:

a phenyl group, a biphenyl group, and a terphenyl group;

a phenyl group, a biphenyl group, and a terphenyl group, each substituted with at least one selected from deuterium, a $C_1$-$C_{20}$ alkyl group, and a $C_1$-$C_{20}$ alkoxy group, $R_5$ in Formulae 2A-1 to 2A-5 is selected from:

hydrogen, deuterium, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one deuterium, and

* in Formulae 2A-1 to 2A-5 and 2B indicates a binding site to a neighboring atom.

2. The organic light-emitting device of claim 1, wherein $Ar_2$ is one selected from groups represented by Formulae 2B-1 to 2B-6:

Formula 2B-1
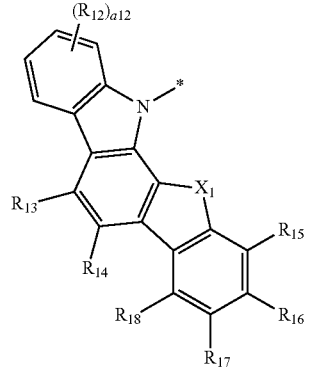

Formula 2B-2
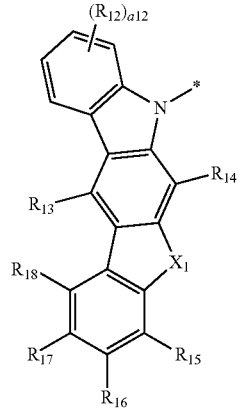

-continued

Formula 2B-3
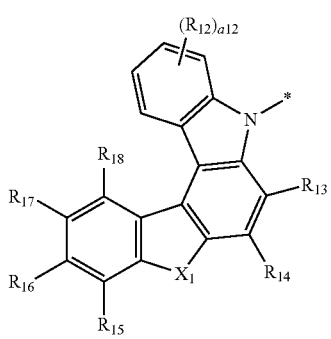

Formula 2B-4
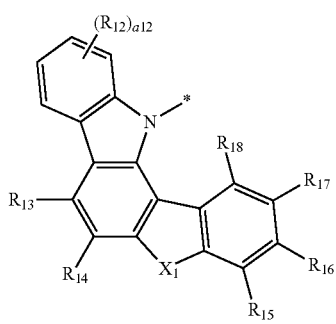

Formula 2B-5
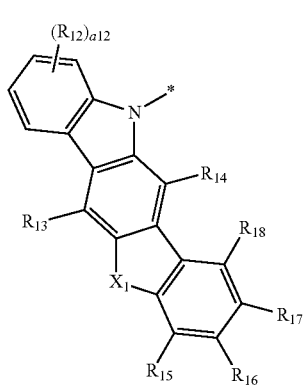

Formula 2B-6
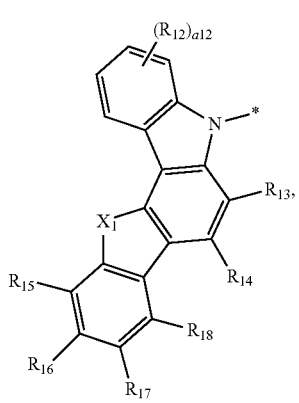

wherein, in Formulae 2B-1 to 2B-6,
$X_1$ is O or S,
$R_{12}$ and a12 are each independently the same as in claim 1,
$R_{13}$ to $R_{18}$ are each independently the same as $R_{11}$ in claim 1, and
* indicates a binding site to a neighboring atom.

3. The organic light-emitting device of claim 1, wherein $R_1$ to $R_3$, $R_{11}$, and $R_{12}$ are each independently selected from:

hydrogen, deuterium, a $C_1$-$C_{10}$ alkyl group, a $C_1$-$C_{10}$ alkoxy group, a phenyl group, a biphenyl group, and a terphenyl group;
a $C_1$-$C_{10}$ alkyl group and a $C_1$-$C_{20}$ alkoxy group, each substituted with at least one deuterium; and
a phenyl group, a biphenyl group, and a terphenyl group, each substituted with at least one selected from deuterium, a $C_1$-$C_{20}$ alkyl group, a $C_1$-$C_{20}$ alkoxy group, a phenyl group, a biphenyl group, and a terphenyl group.

4. The organic light-emitting device of claim 1, wherein $R_4$ is one selected from groups represented by Formulae 3-1 to 3-7:

Formula 3-1
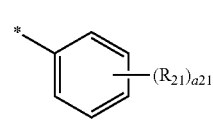

Formula 3-2
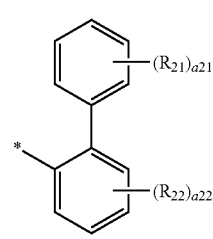

Formula 3-3
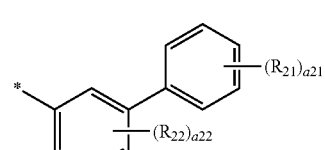

Formula 3-4
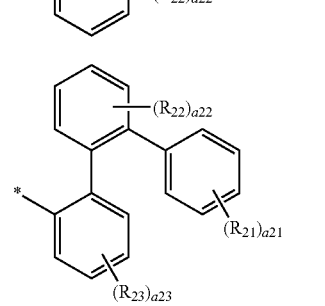

Formula 3-5
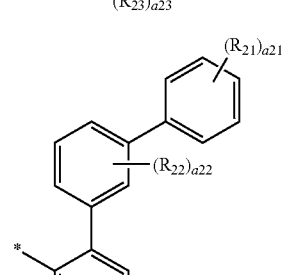

Formula 3-6
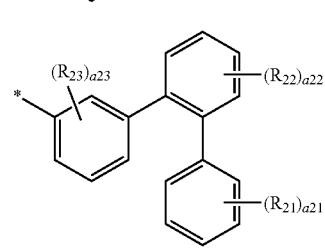

Formula 3-7

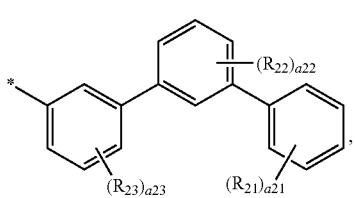

wherein, in Formulae 3-1 to 3-7, $R_{21}$ to $R_{23}$ are each independently hydrogen, deuterium, a $C_1$-$C_{10}$ alkyl group, or a $C_1$-$C_{10}$ alkoxy group, a21 is an integer selected from 0 to 5, a22 and a23 are each independently an integer selected from 0 to 4, and

* indicates a binding site to a neighboring atom.

5. The organic light-emitting device of claim 1, wherein $R_5$ is hydrogen, deuterium, a $C_1$-$C_{10}$ alkyl group, or a $C_1$-$C_{10}$ alkoxy group.

6. The organic light-emitting device of claim 1, wherein the condensed cyclic compound is represented by one selected from Formulae 1-1 to 1-4:

Formula 1-1

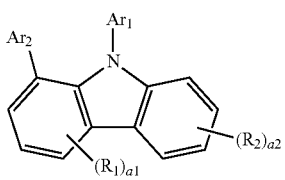

Formula 1-2

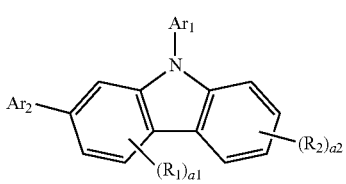

Formula 1-3

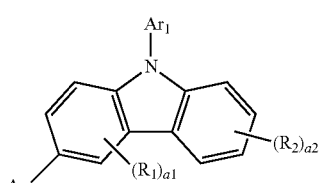

Formula 1-4

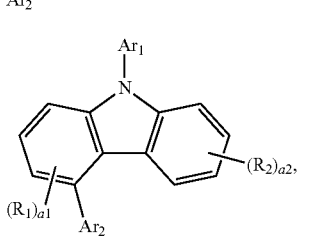

wherein, in Formulae 1-1 to 1-4, $Ar_1$, $A_2$, $R_1$, $R_2$, a1, and a2 are each independently the same as in claim 1.

7. The organic light-emitting device of claim 6, wherein, in Formulae 2A-1 to 2A-5, $R_4$, $R_{4a}$, and $R_{4b}$ are each independently selected from groups represented by Formulae 3-1 to 3-7

Formula 3-1

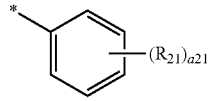

Formula 3-2

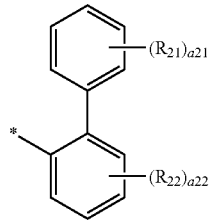

Formula 3-3

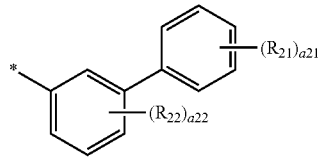

Formula 3-4

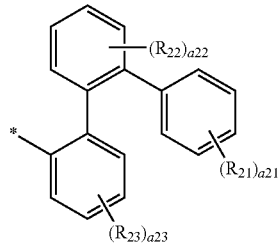

Formula 3-5

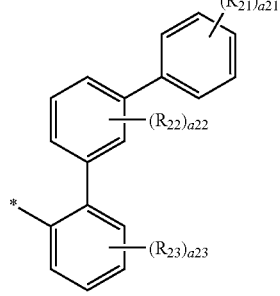

Formula 3-6

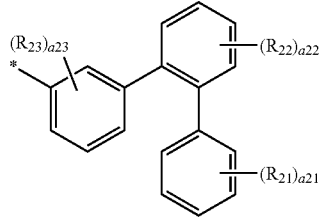

Formula 3-7

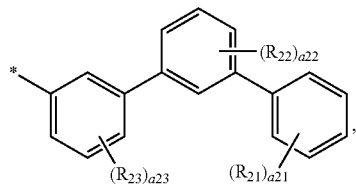

wherein, in Formulae 3-1 to 3-7, $R_{21}$ to $R_{23}$ are each independently hydrogen, deuterium, a $C_1$-$C_{10}$ alkyl group, or a $C_1$-$C_{10}$ alkoxy group, a21 is an integer selected from 0 to 5, a22 and a23 are each independently an integer selected from 0 to 4, and

* indicates a binding site to a neighboring atom.

8. The organic light-emitting device of claim 7, wherein Ar$_2$ is one selected from groups represented by Formulae 2B-1 to 2B-6:

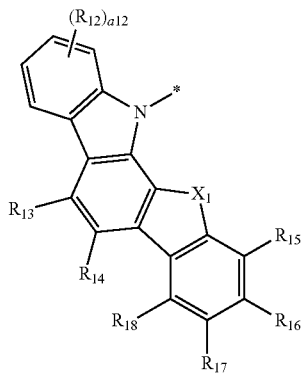

Formula 2B-1

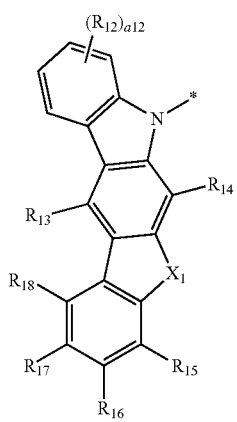

Formula 2B-2

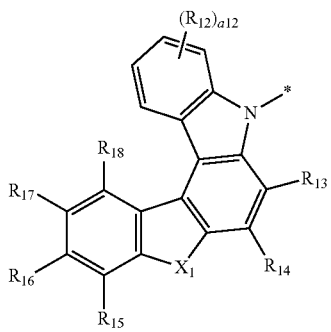

Formula 2B-3

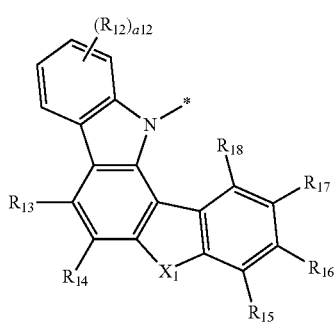

Formula 2B-4

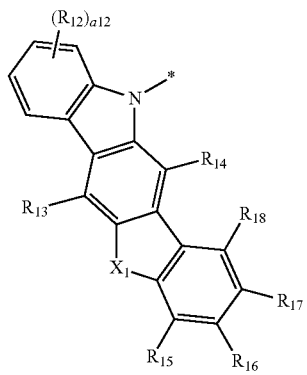

Formula 2B-5

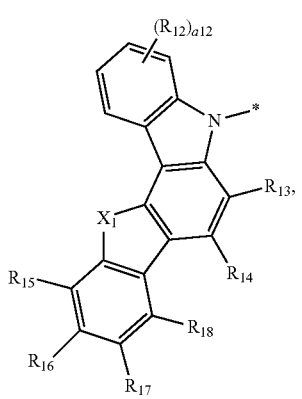

Formula 2B-6 wherein, in Formulae 2B-1 to 2B-6,

X$_1$ is O or S,

R$_{12}$ and a12 are each independently the same as in claim 1,

R$_{13}$ to R$_{18}$ are each independently the same as R$_{11}$ in claim 1, and

* indicates a binding site to a neighboring atom.

9. The organic light-emitting device of claim 8, wherein R$_{12}$ to R$_{18}$ are each independently selected from:

hydrogen, deuterium, a C$_1$-C$_{10}$ alkyl group, a C$_1$-C$_{10}$ alkoxy group, a phenyl group, a biphenyl group, and a terphenyl group;

a C$_1$-C$_{10}$ alkyl group and a C$_1$-C$_{10}$ alkoxy group, each substituted with at least one deuterium; and a phenyl group, a biphenyl group, and a terphenyl group, each substituted with at least one selected from deuterium, a C$_1$-C$_{20}$ alkyl group, a C$_1$-C$_{20}$ alkoxy group, a phenyl group, a biphenyl group, and a terphenyl group.

10. The organic light-emitting device of claim 1, wherein the condensed cyclic compound has an absolute value of a highest occupied molecular orbital in a range of about 5.0 electron volts to about 5.3 electron volts.

11. The organic light-emitting device of claim 1, wherein the condensed cyclic compound has a triplet energy level of about 2.8 electron volts or more.

12. The organic light-emitting device of claim 1, wherein the condensed cyclic compound is one selected from Compounds 1 to 11:

111
1
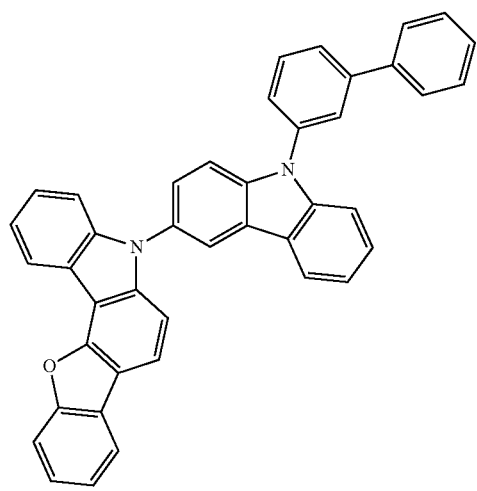
2
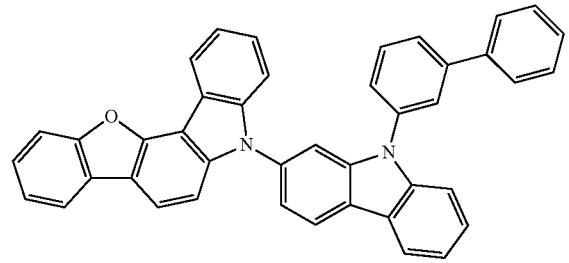
3
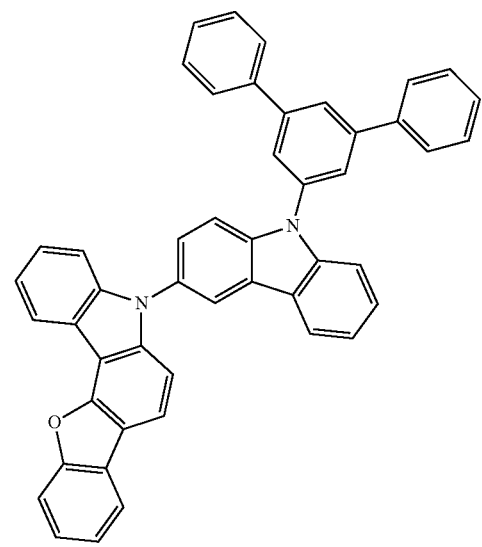
112
-continued
4
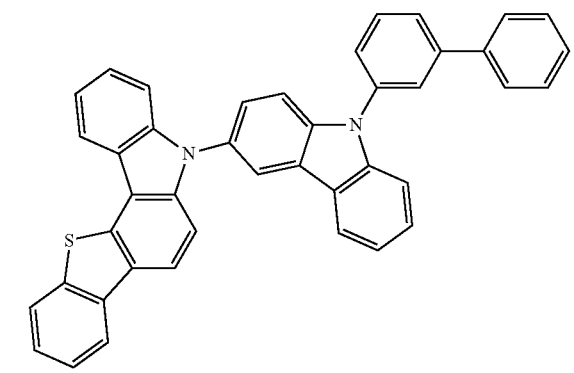
5
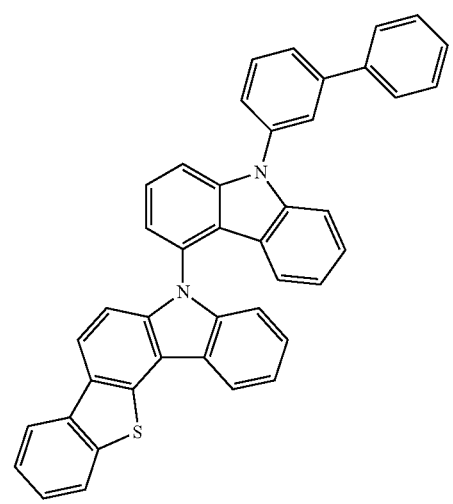
6
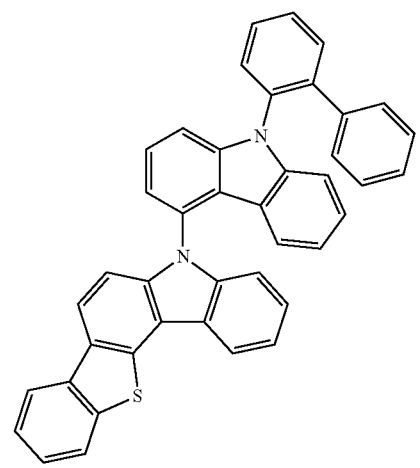

13. The organic light-emitting device of claim 1, wherein the organic layer further comprises an electron transport region disposed between the emission layer and the second electrode, wherein the electron transport region comprises a hole blocking layer, an electron transport layer, an electron injection layer, or a combination thereof.

14. The organic light-emitting device of claim 1, wherein the emission layer comprises the condensed cyclic compound represented by Formula 1.

15. The organic light-emitting device of claim 1, wherein the emission layer further comprises a phosphorescent dopant, wherein the phosphorescent dopant comprises an organometallic compound represented by Formula 81:

$$M(L_{81})_{n81}(L_{82})_{n82} \quad \text{Formula 81}$$

Formula 81A wherein, in Formulae 81 and 81A,
M is selected from iridium (Ir), platinum (Pt), osmium (Os), titanium (Ti), zirconium (Zr), hafnium (Hf), europium (Eu), terbium (Tb), thulium (Tm), and rhodium (Rh),
$L_{81}$ is a ligand represented by Formula 81A, wherein n81 is an integer selected from 1 to 3, and when n81 is two or more, two or more groups $L_{81}$ are identical to or different from each other,
$L_{82}$ is an organic ligand, wherein n82 is an integer selected from 0 to 4, and when n82 is two or more, two or more groups $L_{82}$ are identical to or different from each other,
$Y_{81}$ to $Y_{84}$ are each independently C or N,
$Y_{81}$ and $Y_{82}$ are linked to each other via a single bond or a double bond, and $Y_{83}$ and $Y_{84}$ are linked to each other via a single bond or a double bond, $CY_{81}$ and $CY_{82}$ are each independently selected from a $C_5$-$C_{30}$ carbocyclic group and a $C_1$-$C_{30}$ heterocarbocyclic group, $CY_{81}$ and $CY_{82}$ are optionally further linked to each other via an organic linking group, $R_{81}$ to $R_{85}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{81})(Q_{82})(Q_{83})$, —$N(Q_{84})(Q_{85})$, —$B(Q_{86})(Q_{87})$, and —$P(=O)(Q_{88})(Q_{89})$, a81 to a83 are each independently an integer selected from 0 to 5, wherein, when a81 is two or more, two or more groups $R_{81}$ are identical to or different from each other, when a82 is two or more, two or more groups $R_{82}$ are identical to or different from each other, when a81 is two or more, two or more neighboring groups $R_{81}$ are optionally linked to each other to form a saturated or unsaturated ring, and when a82 is two or more, two or more groups $R_{82}$ are optionally linked to each other to form a saturated or unsaturated ring,

* and *' in Formula 81A each indicate a binding site to M of Formula 81, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{91})(Q_{92})(Q_{93})$, and $Q_{81}$ to $Q_{89}$ and $Q_{91}$ to $Q_{93}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

16. The organic light-emitting device of claim 15, wherein, in Formula 81A, at least one selected from $R_{81}$ in the number of a81 and $R_{82}$ in the number of a82 is a cyano group or deuterium.

17. The organic light-emitting device of claim 14, wherein the emission layer emits blue light.

18. The organic light-emitting device of claim 1, wherein the hole transport region further comprises a hole injection layer, a hole transport layer, or a combination thereof.

19. A condensed cyclic compound represented by Formula 1:

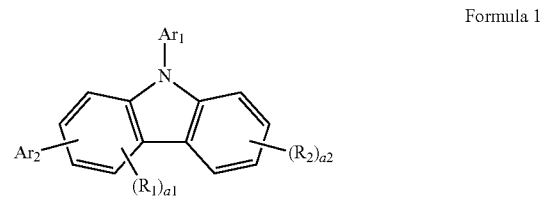

Formula 1

Formula 2A-1

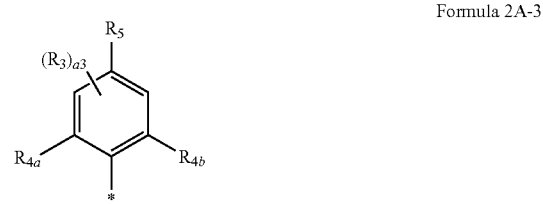

Formula 2A-3

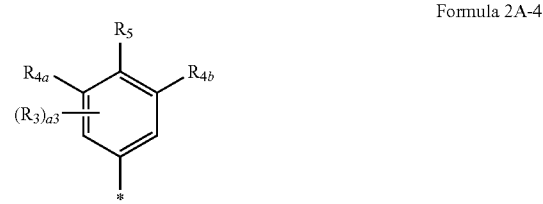

Formula 2A-4

-continued

Formula 2A-5

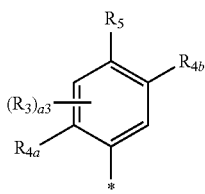

Formula 2B

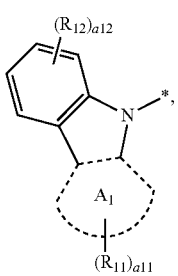

wherein, in Formula 1, $Ar_1$ is one selected from groups represented by Formulae 2A-1, 2A-3, 2A-4 and 2A-5, and $Ar_2$ is a group represented by Formula 2B, ring $A_1$ in Formula 2B is a dibenzofuran ring or a dibenzothiophene ring, $R_1$ to $R_3$, $R_{11}$, and $R_{12}$ in Formulae 1, 2A-1, 2A-3, 2A-4, 2A-5 and 2B are each independently selected from:

hydrogen, deuterium, a $C_1$-$C_{20}$ alkyl group, a phenyl group, a biphenyl group and a terphenyl group;

a $C_1$-$C_{20}$ alkyl group substituted with at least one deuterium; and a phenyl group, a biphenyl group and a terphenyl group, each substituted with at least one selected from deuterium, a $C_1$-$C_{20}$ alkyl group, a phenyl group, a biphenyl group and a terphenyl group, a1 and a3 in Formulae 1, 2A-1, 2A-3, 2A-4 and 2A-5 are each independently an integer selected from 0 to 2, wherein, when a1 is two or more, two or more groups $R_1$ are identical to or different from each other, and when a3 is two or more, two or more groups $R_3$ are identical to or different from each other, a2 and a12 in Formulae 1 and 2B are each independently an integer selected from 0 to 4, wherein, when a2 is two or more, two or more groups $R_2$ are identical to or different from each other, and when a12 is two or more, two or more groups $R_{12}$ are identical to or different from each other, a11 in Formula 2B is an integer selected from 0 to 6, wherein, when a11 is two or more, two or more groups $R_{11}$ are identical to or different from each other, $R_4$, $R_{4a}$ and $R_{4b}$ in Formula 2A-1, 2A-3, 2A-4 and 2A-5 are each independently selected from:

a phenyl group, a biphenyl group, and a terphenyl group;

a phenyl group, a biphenyl group, and a terphenyl group, each substituted with at least one selected from deuterium and a $C_1$-$C_{20}$ alkyl group, $R_5$ in Formulae 2A-1, 2A-3, 2A-4 and 2A-5 is selected from:

hydrogen, deuterium and a $C_1$-$C_{20}$ alkyl group; and a $C_1$-$C_{20}$ alkyl group substituted with at least one deuterium, and \* in Formulae 2A-1, 2A-3, 2A-4, 2A-5 and 2B indicates a binding site to a neighboring atom.

20. A condensed cyclic compound represented by Formula 1.

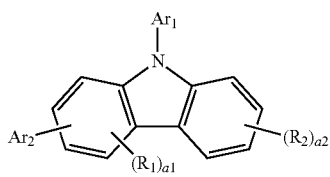

Formula 1

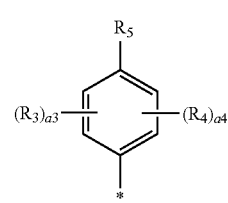

Formula 2A

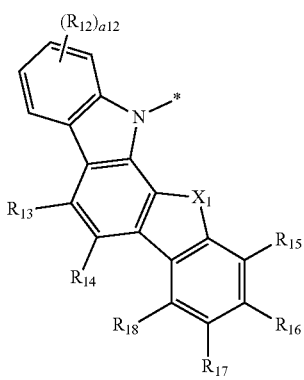

Formula 2B-1

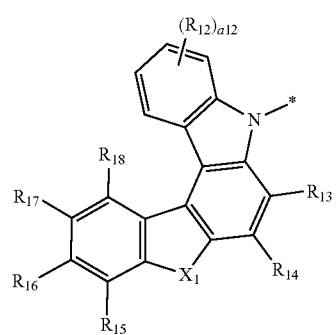

Formula 2B-3

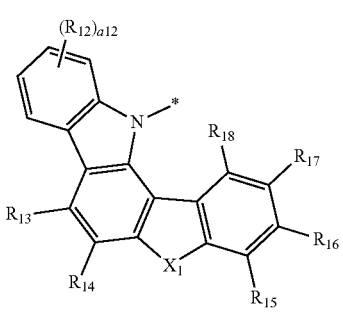

Formula 2B-4

-continued

Formula 2B-5

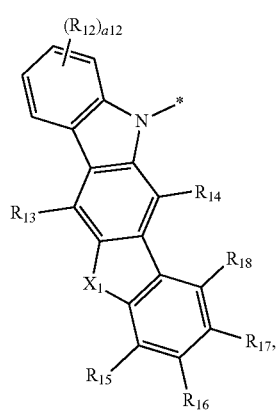

wherein, in Formula 1, Ar₁ is a group represented by Formula 2A, and Ar₂ is one selected from groups represented by Formula 2B-1, 2B-3, 2B-4 and 2B-5, $X_1$ in Formula 2B-1, 2B-3, 2B-4 and 2B-5 is O or S, $R_1$ to $R_3$ and $R_{12}$ to $R_{18}$ in Formulae 1, 2A, 2B-1, 2B-3, 2B-4 and 2B-5 are each independently selected from:

hydrogen, deuterium, a $C_1$-$C_{20}$ alkyl group, a phenyl group, a biphenyl group and a terphenyl group;

a $C_1$-$C_{20}$ alkyl group substituted with at least one deuterium; and a phenyl group, a biphenyl group and a terphenyl group, each substituted with at least one selected from deuterium, a $C_1$-$C_{20}$ alkyl group, a phenyl group, a biphenyl group and a terphenyl group, a1 and a3 in Formulae 1 and 2A are each independently an integer selected from 0 to 3, wherein, when a1 is two or more, two or more groups $R_1$ are identical to or different from each other, and when a3 is two or more, two or more groups $R_3$ are identical to or different from each other, a2 and a12 in Formulae 1, 2B-1, 2B-3, 2B-4 and 2B-5 are each independently an integer selected from 0 to 4, wherein, when a2 is two or more, two or more groups $R_2$ are identical to or different from each other, and when a12 is two or more, two or more groups $R_{12}$ are identical to or different from each other, $R_4$ in Formula 2A is selected from:

a phenyl group, a biphenyl group, and a terphenyl group;

a phenyl group, a biphenyl group, and a terphenyl group, each substituted with at least one selected from deuterium and a $C_1$-$C_{20}$ alkyl group, a4 in Formula 2A is an integer selected from 1 to 4, wherein, when a4 is two or more, two or more groups $R_4$ are identical to or different from each other, $R_5$ in Formula 2A is selected from:

hydrogen, deuterium and a $C_1$-$C_{20}$ alkyl group; and a $C_1$-$C_{20}$ alkyl group substituted with at least one deuterium, and

* in Formulae 2A, 2B-1, 2B-3, 2B-4 and 2B-5 indicates a binding site to a neighboring atom.

21. A condensed cyclic compound being selected from Compounds 1, 2, 4, 5, and 7:

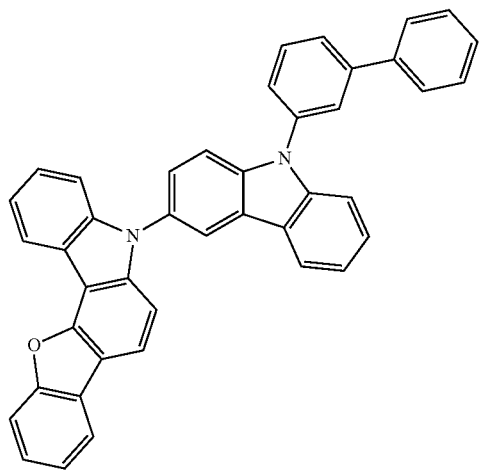

1

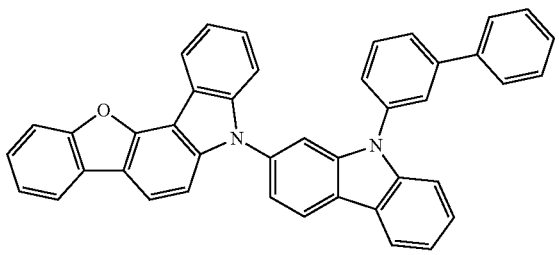

2

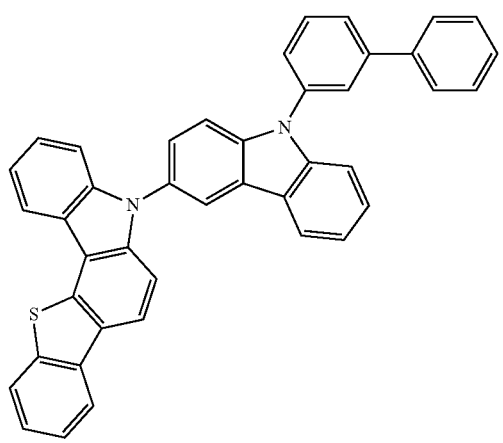

4

121
-continued
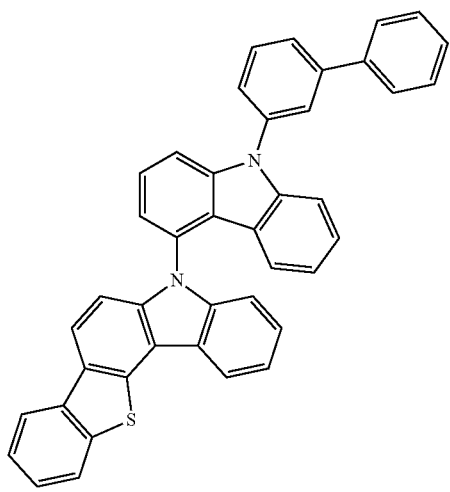
122
-continued
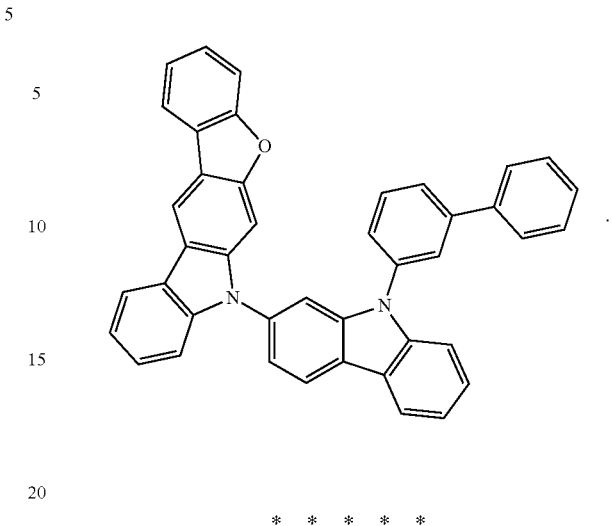
* * * * *